(12) United States Patent
Tarasova et al.

(10) Patent No.: US 9,540,427 B2
(45) Date of Patent: Jan. 10, 2017

(54) PEPTIDE-BASED STAT INHIBITOR

(75) Inventors: Nadya I. Tarasova, Frederick, MD (US); Olga Timofeeva, North Potomac, MD (US); Vadim Gaponenko, Naperville, IL (US); Christopher J. Michejda, North Potomac, MD (US); Maria Michejda, legal representative, North Potomac, MD (US); Alan O. Perantoni, Fairfield, PA (US); Sergey G. Tarasov, Frederick, MD (US)

(73) Assignee: The United States of America, as represented by the Secretary, Department of Health & Human Services, Washington, DC (US)

( * ) Notice: Subject to any disclaimer, the term of this patent is extended or adjusted under 35 U.S.C. 154(b) by 848 days.

(21) Appl. No.: 12/601,711

(22) PCT Filed: May 30, 2008

(86) PCT No.: PCT/US2008/065352
§ 371 (c)(1),
(2), (4) Date: Feb. 5, 2010

(87) PCT Pub. No.: WO2008/151037
PCT Pub. Date: Dec. 11, 2008

(65) Prior Publication Data
US 2010/0184697 A1    Jul. 22, 2010

Related U.S. Application Data

(60) Provisional application No. 60/940,916, filed on May 30, 2007.

(51) Int. Cl.
  *C07K 7/08*   (2006.01)
  *C07K 14/47*  (2006.01)
  *A61K 38/04*  (2006.01)

(52) U.S. Cl.
  CPC ......... *C07K 14/4705* (2013.01); *A61K 38/04* (2013.01)

(58) Field of Classification Search
  None
  See application file for complete search history.

(56) References Cited

U.S. PATENT DOCUMENTS

| | | | | |
|---|---|---|---|---|
| 6,087,478 | A * | 7/2000 | Vinkemeier | C07K 14/4705 435/69.1 |
| 6,368,828 | B1 * | 4/2002 | LaRochelle et al. | 435/69.1 |
| 6,960,647 | B2 | 11/2005 | Zhang et al. | |
| 2001/0046502 | A1 * | 11/2001 | Mokyr | 424/277.1 |
| 2002/0009469 | A1 * | 1/2002 | Berd | 424/277.1 |
| 2004/0009571 | A1 | 1/2004 | Kuriyan et al. | |
| 2004/0031072 | A1 * | 2/2004 | La Rosa et al. | 800/278 |
| 2005/0004009 | A1 | 1/2005 | Turkson et al. | |

FOREIGN PATENT DOCUMENTS

| | | |
|---|---|---|
| WO | WO 01/16605 A2 | 3/2001 |
| WO | WO 01/53455 * | 7/2001 |

OTHER PUBLICATIONS

Q5D0T1 retreived from http://www.uniprot.org/uniprot/Q5D0T1 on Feb. 25, 2013, 5 pages.*
Kang et al ('Comprehensive meta-analysis of signal transducers and activators of transcription (STAT) genomic binding patterns discerns cell-specific cis-regulatory modules' BMC Genomics v14:4 2013 pp. 1-11).*
Blast search (retrieved from http://blast.ncbi.nlm.nih.gov/Blast.cgi on Mar. 2, 2016, 8 pages).*
Byrd et al., *Proc. Amer. Assoc. Can. Res.*, 43, 139 (2002).
Chen et al., *Protein Sci.*, 12, 361-365 (2003).
Haskard et al., *J. Immunol. Methods*, 74 (2), 361-367 (1984).
Huse et al., *Science*, 246, 1275-1281 (1989).
Ivanova et al., *J. Mol. Biol.*, 340, 641-653 (2004).
Knappik et al., *J. Mol. Biol.*, 296, 57-86 (2000).
Köhler et al., *Eur. J. Immunol.*, 6, 511-519 (1976).
Liao et al, *PNAS*, 97 (10), 5267-5272 (2000).
Nagel-Wolfrum et al., *Mol. Cancer Research*, 2, 170-182 (2004).
Phillips et al., *Biomed. Chromatography*, 17, 182-187 (2003).
Roder et al., *Methods Enzymol.*, 121, 140-67 (1986).
Schlessinger et al., *Cancer Res.*, 65, 5828-5834 (2005).
Stolzenberger et al., *Eur. J. Biochem.*, 268, 4809-4814 (2001).
Takeda et al., *J. Endocrinol.*, 159, 323-330 (1998).
Timofeeva et al., *Abstract submitted in connection with Keystone symposia*, Steamboat Springs, Co. (Jan. 5-10, 2007).
Timofeeva et al., *ACS Chem Bio.*, 2 (12), 799-809 (2007).
Timofeeva et al., *Oncogene*, 25 (58), 7555-7564 (2006).
Turkson et al., *JBC*, 276 (48), 45443-45455 (2001).
Turkson et al., *Mol. Cancer Therapies*, 3 (3), 261-269 (2004).
Vinkemeier et al., *Science*, 279 (5353), 1048-1052 (1998).
Yang et al., *Cancer Res.*, 65 (3), 939-947 (2005).
Zhang et al., *Mol. Cell Biochem.*, 288, 179-189 (2006).
Calbiochem, Catalog No. 573096 (revised Dec. 8, 2003).
Unigene Accession Hs. 80642 (printed Nov. 24, 2009).
Unigene Accession Hs. 437058 (printed Nov. 24, 2009).
Unigene Accession Hs. 463059 (printed Nov. 24, 2009).
Unigene Accession Hs. 524518 (printed Nov. 24, 2009).
Unigene Accession Hs. 530595 (printed Nov. 24, 2009).
Unigene Accession Hs. 632256 replaced by Hs. 721627 (printed Nov. 24, 2009).
Unigene Accession Hs. 642990 (printed Nov. 24, 2009).

* cited by examiner

*Primary Examiner* — Karlheinz R Skowronek
*Assistant Examiner* — Ronald Niebauer
(74) *Attorney, Agent, or Firm* — Bryan D. Zerhusen; Locke Lord LLP

(57) ABSTRACT

A peptide or peptidomimetic comprising the amino acid sequence of the second helix of a STAT protein, or a variant of such sequence, wherein the peptide or peptidomimetic comprises about 40 or fewer amino acids and binds to a STAT protein, as well as a method of inhibiting a STAT protein in a cell, a method of treating or preventing a disease associated with STAT overexpression in a host, and related compounds, compositions, and methods.

14 Claims, No Drawings

PEPTIDE-BASED STAT INHIBITOR

CROSS-REFERENCE TO RELATED APPLICATIONS

This patent application is a U.S. National Phase of International Patent Application No. PCT/US08/65352, filed May 30, 2008, which claims the benefit of U.S. Provisional Patent Application No. 60/940,916, filed May 30, 2007.

Incorporated by reference in its entirety herein is a computer-readable nucleotide/amino acid sequence listing submitted concurrently herewith and identified as follows: One 23,594 Byte ASCII (Text) file named "705512ST25-2.TXT" created on Feb. 8, 2013.

BACKGROUND OF THE INVENTION

The deregulation of Signal Transducers and Activators of Transcription (STAT) pathways occurs during development of many types of tumors. Among STAT family members, aberrant activation of STAT3 is most frequent in almost all blood malignancies and solid tumors, including lymphomas and leukemias, breast, prostate, lung, head and neck, brain and colon cancers. Thus, the STAT family of proteins, particularly STAT3, is a promising target for the development of novel anticancer drugs.

STAT3 is believed to be activated in the cytoplasm by tyrosine phosphorylation in response to stimulation with growth factors and cytokines. Phosphorylation triggers dimerization and translocation to the nucleus followed by binding to STAT-specific DNA-response elements in the promoters of target genes. Dephosphorylated STAT3 is released from DNA and returns to the cytoplasm. Among the known major STAT3 target genes are those that control cell cycle progression and growth, survival, angiogenesis, motility, and differentiation. STAT3 activation is normally transient and tightly regulated, as is the expression of its target genes. Constitutively active STAT3 induces deleteriously prolonged activation of some target genes, thus contributing to tumor growth and progression.

Most currently available STAT inhibitors target the abnormally activated kinases upstream of STAT. However, direct inhibitors of STAT offer greater selectivity. Thus, there remains a desire for additional STAT inhibitors, especially direct inhibitors of STAT.

BRIEF SUMMARY OF THE INVENTION

The invention provides an isolated or purified peptide or peptidomimetic comprising the amino acid sequence of the second helix of a STAT protein, or a variant of such sequence, wherein the peptide or peptidomimetic comprises no more than about 40 amino acids and binds to a STAT protein. The invention also provides a cell comprising the peptide or peptidomimetic, a nucleic acid encoding the amino acid sequence of the peptide or peptidomimetic, and an antibody that binds to the peptide or peptidomimetic.

The invention further provides a method of inhibiting a STAT protein in a cell, which methods comprises introducing the peptide or peptidomimetic into the cell, whereby a STAT protein is inhibited.

The invention also provides a method of treating or preventing a disease associated with STAT overexpression in a host comprising administering to the host the peptide or peptidomimetic, whereby the disease associated with STAT overexpression is treated or prevented.

Additionally, the invention provides a method of screening for a STAT protein inhibitor using the peptide or peptidomimetic. In one aspect of the invention, the method comprises (a) combining a STAT protein, the peptide or peptidomimetic, and a test compound, (b) detecting binding of the STAT protein to the peptide or peptidomimetic in the presence of the test compound, and (c) comparing binding of the STAT protein to the peptide or peptidomimetic in the presence of the test compound to binding of the STAT protein to the peptide or peptidomimetic in the absence of the test compound, wherein a decrease in binding of the STAT protein to the peptide or peptidomimetic in the presence of the test compound as compared to such binding in the absence of the test compound indicates that the test compound is a STAT inhibitor candidate. In a related aspect, the method of screening for a STAT inhibitor comprises (a) combining a test compound and the peptide or peptidomimetic, and (b) detecting binding of the test compound to the peptide or peptidomimetic, wherein binding of the test compound to the peptide or peptidomimetic indicates that the test compound is a STAT inhibitor candidate.

Related compounds, compositions, and methods also are provided, as will be apparent from the detailed description of the invention.

DETAILED DESCRIPTION OF THE INVENTION

The invention provides a peptide or peptidomimetic that binds to a STAT protein and, preferably, inhibits one or more activities of STAT proteins, particularly activities of STAT proteins that involve the N-terminal domain of STAT. The family of STAT proteins includes STAT1 (UniGene Accession Hs.642990), STAT2 (UniGene Accession Hs. 530595), STAT3 (UniGene Accession Hs.463059), STAT4 (UniGene Accession Hs.80642), STAT5a (UniGene Accession Hs.437058), STAT5b (UniGene Accession Hs.632256), and STAT6 (UniGene Accession Hs.524518). The N-terminal domain of a STAT protein typically is considered to be the region of about 135 contiguous amino acids that includes the N-terminal amino acid. The peptide or peptidomimetic comprises about 40 or fewer amino acid residues, and includes the amino acid sequence of the second helix of a STAT protein (also referred to herein as "helix 2" of a STAT protein), or a variant of such sequence provided that the variation does not abolish the peptide or peptidomimetic's STAT-inhibitory properties.

The second helix of STAT includes approximately 12 residues of the N-terminal domain of the STAT protein located from about residue 11 to about residue 22 (numbering residues from the N-terminus of the protein). Partial sequences of the N-terminal domains of several STAT proteins are provided in Table 1, wherein the second helix regions are underlined.

TABLE 1

| STAT Protein | Partial Sequence of STAT N-Terminal Domain Showing Second Helix |
|---|---|
| STAT1 (SEQ ID NO: 1) | MSQWYELQQLDSKFLEQVHQLYDDSFPMEIRQYLAQWLEKQDWEH |
| STAT2 (SEQ ID NO: 2) | MAQWEMLQNLDSPFQDQLHQLYSHSLLPVDIRQYLAVWIEDQNWQ |
| STAT 3 (SEQ ID NO: 3) | MAQWNQLQQLDTRYLEQLHQLYSDSFPMELRQFLAPWIESQDWAY |

TABLE 1-continued

| STAT Protein | Partial Sequence of STAT N-Terminal Domain Showing Second Helix |
|---|---|
| STAT4 (SEQ ID NO: 4) | MSQWNQVQQL<u>EIKFLEQVDQFYDDNFPMEIRHLLA</u> QWIENQDWEA |
| STAT5A (SEQ ID NO: 5) | MAGWIQAQQL<u>QGDALRQMQVLYGQHFPIEVRHYLA</u> QWIESQPWDA |
| STAT5B (SEQ ID NO: 6) | MAVWIQAQQL<u>QGEALHQMQALYGQHFPIEVRHYLS</u> QWIESQAWDS |
| STAT6 (SEQ ID NO: 7) | MSLWGLVSKM <u>PPEKVQR LYVDFPQHLRHLLGDW</u> LESQPWEFLVGS |

Without wishing to be bound by any particular theory, it is believed that the peptide or peptidomimetic binds to a region of the N-terminal domain of the STAT protein, thereby inhibiting at least some N-terminal functions of STAT proteins. The N-terminal domain of STAT3 is believed to be involved in many protein-protein interactions, including the interaction of two STAT proteins to form a dimer (STAT-STAT dimerization); the interaction of two STAT dimers, e.g., on neighboring DNA sites, to form a more stable tetramer (tetramerzation); the interaction of a STAT protein with other transcription factors and cofactors, for example, to form enhanceosomes; and the interaction of STAT with histone-modifier proteins to induce changes in chromatin structure. These complex interactions provide for maximum STAT-dependent transcriptional stimulation. The N-terminal domain also has been implicated in receptor binding and nuclear translocation of STATs. Thus, the peptide or peptidomimetic preferably inhibits one or more of the above STAT functions, especially STAT-STAT protein dimerization and/or tetramerzation, and STAT-DNA interaction.

A peptide or peptidomimetic is considered to inhibit the function of a STAT protein if, in the presence of the peptide or peptidomimetic, STAT binding to a STAT target (e.g., another STAT protein, a protein other than STAT, or a nucleic acid) is reduced to any degree as compared to the binding of STAT to the same target in the absence of the peptide or peptidomimetic. Preferably, the peptide or peptidomimetic inhibits STAT activity to a degree sufficient to inhibit STAT regulation of genes, reduce the rate of cell growth of a cancer cell, and/or induce cell death of a cancer cell. Gene targets of STAT may include Activating transcription factor 3 (ATF3), Axin1 up-regulated 1 (AXU1), Nuclear receptor subfamily 4 group A member 1 (NR4A1), Basic helix-loop-helix domain containing, class 2 (STRA13), Growth arrest and DNA damage-inducible, alpha (GADD45A), Cell death-inducing DFFA-like effector B (CIDEB), FBJ murine osteosarcoma viral oncogene homolog B (FOSB), Dual specificity phosphatases 4 (DUSP4), Early growth response 2 (EGR2) and 3 (EGR3), CDC-like kinase-1 (CLK-1). Thus, the peptide or peptidomimetic can be used to regulate (e.g., upregulate or downregulate) the expression of such genes. STAT targets also may include histone deacetylases (e.g., HDAC1) and DNA methyltransferases (e.g., DNMT1), and the peptide or peptidomimetic can be used to inhibit the binding or other interaction between a STAT protein (e.g., STAT3) and one or both of these targets. Suitable assays to test for such binding activity and inhibition are known in the art, including binding affinity assays, cell growth and cytotoxicity assays, and gene regulation assays (e.g., luciferase reporter assay). Some of these types of tests are illustrated in the Examples provided herein.

The sequence of the second helix of any STAT protein can be used as a basis for the peptide or peptidomimetic. According to one aspect of the invention, the peptide or peptidomimetic comprises the amino acid sequence of the second helix of STAT3, or variant thereof. Such a peptide, preferably, binds at least to STAT3, although it may also bind to other STAT proteins. By way of illustration, SEQ ID NOs: 8-11 and 35-38 (inverse sequences) are based upon the second helix of STAT3, but incorporate several positions of variability indicated by an "X" in the sequence. The positions of the sequence indicated by an "X" can be substituted with any amino acid residue, provided that it does not eliminate the ability of the peptide or peptidomimetic to bind to a STAT protein, particularly STAT3, and/or inhibit the function of such protein. Table 2 illustrates preferred amino acids to be used at each position of variability represented by an "X". Of course, other amino acid residues can be used instead of the exemplary residues, which are provided for illustration, particularly amino acid residues having chemical properties similar to those of the exemplary residues. Thus, according to this aspect of the invention, the peptide or peptidomimetic can comprise the amino acid sequence of any of SEQ ID NOs: 8-11, or the inverse sequence thereof (e.g., SEQ ID NOs: 35-38). Specific examples of such sequences are provided by SEQ ID NOs: 12-30 and 39-52.

In another aspect of the invention, the peptide or peptidomimetic comprises the amino acid sequence of the second helix of STAT5a or STAT5b, or a variant thereof. The peptide or peptidomimetic according to this aspect of the invention preferably binds to at least STAT5a or STAT5b, although it also may bind to other STAT proteins. Variants of such sequences include, for example, the amino acid sequences encompassed by SEQ ID NOs: 60 and 61, or the inverse sequences thereof (e.g., SEQ ID NOs: 66 and 67), wherein positions of variability are indicated by "X". "X" can be any amino acid. Preferred amino acids include the amino acids indicated in Table 3, as well as other amino acids that have chemical properties similar to the amino acids indicated in Table 3. Specific examples of such sequences include, by way illustration, SEQ ID NOs: 62-65, and 78.

The amino acid sequence of the second helix of STAT1, STAT2, STAT4, or STAT6, or a variant thereof, also can be used as a basis for the peptide or peptidomimetic, in which case the peptide or peptidomimetic preferably binds to at least STAT1, STAT2, STAT4, or STAT6, although it may bind to other STAT proteins. Specific examples of such sequences include, by way of illustration, SEQ ID NOs: 55-59, 68-73, and 75-77.

TABLE 2

| | |
|---|---|
| <u>Xaa</u>-Thr-<u>Xaa</u>-Tyr-Leu-<u>Xaa</u>-<u>Xaa</u>-Leu-His-<u>Xaa</u>-Leu-<u>Xaa</u> | (SEQ ID NO: 8) |
| <u>Xaa</u>-Thr-Arg-Tyr-Leu-<u>Xaa</u>-Gln-Leu-His-Lys-Leu-Tyr | (SEQ ID NO: 9) |
| <u>Xaa</u>-Thr-<u>Xaa</u>-Tyr-Leu-<u>Xaa</u>-<u>Xaa</u>-Leu-His-<u>Xaa</u>-Leu-<u>Xaa</u>-Xaa | (SEQ ID NO: 10) |
| <u>Xaa</u>-Thr-Arg-Tyr-Leu-<u>Xaa</u>-Gln-Leu-His-Lys-Leu-Tyr-Xaa | (SEQ ID NO: 11) |

TABLE 2-continued

| Xaa Position (as applicable) | Preferred Amino Acids |
|---|---|
| 1 | Small amino acids*; Asp, Ala, or Asn |
| 3 | Positively charged amino acids; Arg or Lys |
| 6 | Polar amino acids; neutral and/or negatively charged amino acids; Glu or Gln |
| 7 | Polar amino acids; neutral and/or negatively charged amino acids; Glu or Gln |
| 10 | Positively charged amino acids; Gln, Lys, Diaminobutyric acid (Dab), Ala, or Glu |
| 12 | Aromatic amino acids; Tyr or CyPhen |
| 13 | Positively charged amino acids; Lys, Arg, or Ser |

†-Xaa-Leu-Xaa-His-Leu-Xaa-Xaa-Leu-Tyr-Xaa-Thr-Xaa (SEQ ID NO: 35)

†-Tyr-Leu-Lys-His-Leu-Gln-Xaa-Leu-Tyr-Arg-Thr-Xaa (SEQ ID NO: 36)

Xaa-Xaa-Leu-Xaa-His-Leu-Xaa-Xaa-Leu-Tyr-Xaa-Thr-Xaa (SEQ ID NO: 37)

Xaa-Tyr-Leu-Lys-His-Leu-Gln-Xaa-Leu-Tyr-Arg-Thr-Xaa (SEQ ID NO: 38)

| Xaa Position (as applicable) | Preferred Amino Acids |
|---|---|
| 1 | Positively charged amino acids; Lys, Arg, or Ser |
| 2 | Aromatic amino acids; Tyr or CyPhen |
| 4 | Positively charged amino acid, Gln, Lys, Diaminobutyric acid (Dab), Ala, or Glu |
| 7 | Polar amino acids; neutral and/or negatively charged amino acids; Glu or Gln |
| 8 | Polar amino acids; neutral and/or negatively charged amino acids; Glu or Gln |
| 11 | Positively charged amino acids; Arg or Lys |
| 13 | Small amino acids*; Asp, Ala, or Asn |

†An amino acid at position 1 of SEQ ID NOs: 35 and 36 is not required.
*Molecular mass of about 133 or less.

TABLE 3

Gln-Gly-Xaa-Ala-Leu-Xaa-Gln-Xaa-Gln-Xaa-Leu-Tyr (SEQ ID NO: 60)

Gln-Gly-Asp-Ala-Leu-Arg-Gln-Xaa-Gln-Val-Leu-Tyr (SEQ ID NO: 61)

| Xaa Position (as applicable) | Preferred Amino Acids |
|---|---|
| 3 | Negatively charged amino acids; Asp or Glu |
| 6 | Negatively charged amino acids; Arg or His |
| 8 | Hydrophobic* and/or neutral amino acids; Met or Nle |
| 10 | Hydrophobic, small**, and/or neutral amino acids; Val or Ala |

TABLE 3-continued

Tyr-Leu-Xaa-Gln-Xaa-Gln-Xaa-Leu-Ala-Xaa-Gly-Gln (SEQ ID NO: 66)

Tyr-Leu-Val-Gln-Xaa-Gln-Arg-Leu-Ala-Asp-Gly-Gln (SEQ ID NO: 67)

| Xaa Position (as applicable) | Preferred Amino Acids |
|---|---|
| 3 | Hydrophobic, small**, and/or neutral amino acids; Val or Ala |
| 5 | Hydrophobic* and/or neutral amino acids; Met or Nle |
| 7 | Negatively charged amino acids; Arg or His |

TABLE 3-continued

| 10 | Negatively charged amino acids; Asp or Glu |

*Hydropathy index greater than zero. Kyte, J.; Doolittle, R. F., J. Mol. Biol., 157(1), 105-132 (1982)
**Molecular mass of about 133 or less.

Any of the foregoing sequences can be cyclized by known methods. For instance, cysteine, lysine, and/or glutamic acid residues can be introduced at desired positions of cyclization. Examples of such sequences are provided by SEQ ID NOs: 31-34, which are variants of the second helix of STAT3:

SEQ ID NO: 31
DTKCLEQKHKLYK-ε-Pal
|_____|

SEQ ID NO: 32
DTKYCEQLKKLYKK-ε-Pal
|_____|

SEQ ID NO: 33
DTKCLEQKHKLYK-ε-Pal
|_____|

SEQ ID NO: 34
DTKCLEQKHKLYKK-ε-Pal
|_____|

Variant sequences other than those specifically mentioned herein are contemplated, which comprise significant sequence identity to the amino acid sequence of the second helix of a STAT protein (e.g., 80%, 85%, 90%, 95%, 98%, or 99% sequence identity) and retain the ability to bind to STAT and/or inhibit the function of a STAT protein. Such variants comprise one or more amino acid substitutions, deletions, or insertions as compared to the parent amino acid sequence. Conservative amino acid substitutions are known in the art, and include amino acid substitutions in which one amino acid having certain physical and/or chemical properties is exchanged for another amino acid that has the same or similar chemical or physical properties. For instance, the conservative amino acid substitution can be an acidic amino acid substituted for another acidic amino acid (e.g., Asp or Glu), an amino acid with a nonpolar side chain substituted for another amino acid with a nonpolar side chain (e.g., Ala, Gly, Val, Ile, Leu, Met, Phe, Pro, Trp, Val, etc.), a basic amino acid substituted for another basic amino acid (Lys, Arg, etc.), an amino acid with a polar side chain substituted for another amino acid with a polar side chain (Asn, Cys, Gln, Ser, Thr, Tyr, etc.), etc.

The peptide or peptidomimetic also can comprise synthetic, non-naturally occurring amino acids. Such synthetic amino acids include, for example, aminocyclohexane carboxylic acid, norleucine, α-amino n-decanoic acid, homoserine, S-acetylaminomethyl-cysteine, trans-3- and trans-4-hydroxyproline, 4-aminophenylalanine, 4-nitrophenylalanine, 4-chlorophenylalanine, 4-carboxyphenylalanine, β-phenylserine β-hydroxyphenylalanine, phenylglycine, α-naphthylalanine, cyclohexylalanine, cyclohexylglycine, indoline-2-carboxylic acid, 1,2,3,4-tetrahydroisoquinoline-3-carboxylic acid, aminomalonic acid, aminomalonic acid monoamide, N'-benzyl-N'-methyl-lysine, N',N'-dibenzyl-lysine, 6-hydroxylysine, ornithine, α-aminocyclopentane carboxylic acid, α-aminocyclohexane carboxylic acid, α-aminocycloheptane carboxylic acid, α-(2-amino-2-norbornane)-carboxylic acid, α,γ-diaminobutyric acid, α,β-diaminopropionic acid, homophenylalanine, and α-tert-butylglycine.

The term "peptidomimetic" as used herein refers to a compound that comprises the same general structure of a corresponding polypeptide, but which includes modifications that increase its stability or biological function. For instance, the peptidomimetic can be a "reverso" analogue of a given peptide, which means that the peptidomimetic comprises the reverse sequence of the peptide. In addition, or instead, the peptidomimetic can comprise one or more amino acids in a "D" configuration (e.g., D-amino acids), providing an "inverso" analogue. Peptidomimetics also include peptoids, wherein the side chain of each amino acid is appended to the nitrogen atom of the amino acid as opposed to the alpha carbon. Peptoids can, thus, be considered as N-substituted glycines which have repeating units of the general structure of $NRCH_2CO$ and which have the same or substantially the same amino acid sequence as the corresponding polypeptide.

The peptide or peptidomimetic can comprise the amino acid sequence of the second helix of a STAT protein alone or as part of a larger sequence, which includes additional amino acid residues (e.g., one, two, three, four, five or more amino acid residues) flanking the amino acid sequence of the second helix to the amino-terminal side, carboxy-terminal side, or both. Any flanking sequences can be used, provided the additional amino acid sequences do not eliminate the ability of the peptide to bind to and/or inhibit the function of a STAT protein.

The peptide or peptidomimetic can comprise, consist essentially of, or consist of, any of foregoing sequences or variants thereof. The peptide or peptidomimetic consists essentially of the foregoing sequences if it does not comprise other elements that prevent the peptide from binding to STAT and/or inhibiting one or more STAT functions.

Smaller peptides and peptidomimetics are believed to be advantageous for inhibiting STAT function and to facilitate entry into a cell. Thus, the peptide or peptidomimetic preferably comprises fewer than about 40 amino acids, such as about 35 or fewer amino acids, about 25 or fewer amino acids, or even about 20 or fewer amino acids. Generally, however, the peptide or peptidomimetic will comprise at least about 8 amino acids, such as at least about 10 amino acids, or at least about 15 amino acids.

The peptide or peptidomimetic can be used alone, or it can be coupled to a cell penetrating motif so as to more efficiently facilitate the delivery of the peptide to the interior of a cell. Thus, the peptide or peptidomimetic can be provided as part of a composition comprising the peptide and cell penetrating motif Any of various cell penetrating motifs known in the art can be used. By way of illustration, suitable cell penetrating motifs include lipids and fatty acids, peptide transduction domains (e.g., HIV-TAT, HSV Transcription Factor (VP22), and penetratin), and other types of carrier molecules (e.g., Pep-1).

According to one aspect of the invention, the cell penetrating motif is a fatty acid or lipid molecule. The fatty acid or lipid molecule can be, for example, a palmitoyl group, farnesyl group (e.g., farnesyl diphosphate), a geranylgeranyl group (e.g., geranylgeranyl diphosphate), a phospholipid group, glycophosphatidylinositol, phosphatidylserine, phosphatidylethanolamine, sphingomyelin, phosphatidylcholine, cardiolipin, phosphatidylinositol, phosphatidic acid, lysophosphoglyceride, a cholesterol group, an acetyl group, and the like. Preferably, the fatty acid molecule is a $C_1$ to $C_{24}$ fatty acid, e.g., lauric acid, palmitic acid, myristic acid, stearic acid, oleic acid, linoleic acid, α-linoleic acid, linolenic acid, arachidonic acid, timnodonic acid, docosohexenoic acid, erucic acid, arachidic acid, behenic acid. More preferably, the fatty acid molecule is a $C_8$ to $C_{16}$ fatty acid.

The fatty acid or lipid molecule can be attached to any suitable part of the peptide or peptidomimetic. In a preferred embodiment of the invention, the fatty acid or lipid molecule is attached at the amino (N—) terminus, the carboxyl (C—) terminus, or both the N- and C-termini of the peptide or peptidomimetic. When the fatty acid or lipid molecule is attached at the C-terminus of the polypeptide or peptidomimetic, the fatty acid or lipid molecule preferably is modified, e.g., to include an amino group such as $NH_2(CH_2)_nCOOH$ or $CH_3(CH_2)_mCH(NH_2)COOH$, wherein each of n and m is, independently, 1 to 24, preferably 8 to 16. The fatty acid or lipid residue can advantageously be attached to a terminal lysine in the epsilon (ε) position.

According to another aspect of the invention, the cell penetrating motif is a peptide transduction domain (also known as protein transduction domains or PTDs). PTDs typically are fused to the STAT-inhibitory peptide or peptidomimetic. Thus, the peptide or peptidomimetic can be a fusion protein comprising the peptide or peptidomimetic and a PTD. Often, the fusion protein is cleaved inside of a cell to remove the cell penetrating motif.

The peptide or peptidomimetic can further comprise linking residues disposed between the amino acid sequence comprising the second helix of STAT and the cell penetrating motif. Illustrative examples of such linking residues include K, KK, RK, RQ, KQ, RQI, KQI, RQIK (SEQ ID NO: 79), and KQIK (SEQ ID NO: 80).

The peptide or peptidomimetic can be prepared by any method, such as by synthesizing the peptide or peptidomimetic, or by expressing a nucleic acid encoding an appropriate amino acid sequence in a cell and harvesting the peptide from the cell. Of course, a combination of such methods also can be used. Methods of de novo synthesizing peptides and peptidomimetics, and methods of recombinantly producing peptides and peptidomimetics are known in the art (see, e.g., Chan et al., *Fmoc Solid Phase Peptide Synthesis*, Oxford University Press, Oxford, United Kingdom, 2005; *Peptide and Protein Drug Analysis*, ed. Reid, R., Marcel Dekker, Inc., 2000; *Epitope Mapping*, ed. Westwood et al., Oxford University Press, Oxford, United Kingdom, 2000; Sambrook et al., *Molecular Cloning: A Laboratory Manual*, 3rd ed., Cold Spring Harbor Press, Cold Spring Harbor, N.Y. 2001; and Ausubel et al., *Current Protocols in Molecular Biology*, Greene Publishing Associates and John Wiley & Sons, NY, 1994).

The invention also provides a nucleic acid encoding the amino acid sequence of the peptide or peptidomimetic. The nucleic acid can comprise DNA or RNA, and can be single or double stranded. Furthermore, the nucleic acid can comprise nucleotide analogues or derivatives (e.g., inosine or phosphorothioate nucleotides and the like). The nucleic acid can encode the amino acid sequence of the peptide or peptidomimetic alone, or as part of a fusion protein comprising such sequence and a cell penetrating motif, as described herein. The nucleic acid encoding the amino acid sequence of the peptide or peptidomimetic can be provided as part of a construct comprising the nucleic acid and elements that enable delivery of the nucleic acid to a cell, and/or expression of the nucleic acid in a cell. Such elements include, for example, expression vectors and transcription and/or translation sequences. Suitable vectors, transcription/translation sequences, and other elements, as well as methods of preparing such nucleic acids and constructs, are known in the art (e.g., Sambrook et al., supra; and Ausubel et al., supra).

The present invention further provides an antibody to the peptide or peptidomimetic, or an antigen binding fragment or portion thereof (e.g., Fab, F(ab')$_2$, dsFv, sFv, diabodies, and triabodies). The antibody can be monoclonal or polyclonal, and of any isotype, e.g., IgA, IgD, IgE, IgG, IgM, etc. The antibody can be a naturally-occurring antibody, e.g., an antibody isolated and/or purified from a mammal, e.g., mouse, rabbit, goat, horse, chicken, hamster, human, etc. Alternatively, the antibody can be a synthetic or genetically-engineered antibody, e.g., a humanized antibody or a chimeric antibody. The antibody can be in monomeric or polymeric form. The antibody, or antigen binding portion thereof, can be modified to comprise a detectable label, such as, for instance, a radioisotope, a fluorophore (e.g., fluorescein isothiocyanate (FITC), phycoerythrin (PE)), an enzyme (e.g., alkaline phosphatase, horseradish peroxidase), or element particles (e.g., gold particles). Such antibodies can be used for any purpose, such as to facilitate the detection or purification of a peptide or peptidomimetic described herein. Suitable methods of making antibodies are known in the art, including standard hybridoma methods, EBV-hybridoma methods, bacteriophage vector expression systems, and phage-display systems (see, e.g., Köhler and Milstein, *Eur. J. Immunol.*, 5, 511-519 (1976); Harlow and Lane (eds.), *Antibodies: A Laboratory Manual*, CSH Press (1988); C. A. Janeway et al. (eds.), *Immunobiology*, 5th Ed., Garland Publishing, New York, N.Y. (2001); Haskard and Archer, *J. Immunol. Methods*, 74(2), 361-67 (1984); Roder et al., *Methods Enzymol.*, 121, 140-67 (1986); Huse et al., *Science*, 246, 1275-81 (1989); Sambrook et al., supra; Ausubel et al., supra; Knappik et al., *J. Mol. Biol.* 296: 57-86 (2000)).

The peptide or peptidomimetic, nucleic acid, or antibody can be isolated. The term "isolated" as used herein encompasses compounds or compositions that have been removed from a biological environment (e.g., a cell, tissue, culture medium, body fluid, etc.), or otherwise increased in purity to any degree (e.g., isolated from a synthesis medium). Isolated compounds and compositions, thus, can be synthetic or naturally produced.

A cell comprising the peptide or peptidomimetic, or nucleic acid encoding the amino acid sequence of the peptide or peptidomimetic, also is provided herein. Such a cell includes, for example, a cell engineered to express a nucleic acid encoding the amino acid sequence of the peptide or peptidomimetic. Suitable cells include prokaryotic and eukaryotic cells, e.g., mammalian cells, yeast, fungi, and bacteria (such as *E. coli*). The cell can be in vitro, as is useful for research or for production of the peptide or peptidomimetic, or the cell can be in vivo, for example, in a transgenic mammal that expresses the peptide.

The peptide or peptidomimetic can be used for any purpose, but is especially useful for inhibiting the activity of a STAT protein in a cell. Thus, provided herein is a method of inhibiting a STAT protein in a cell, which method comprises administering a peptide or peptidomimetic described herein to a cell in an amount sufficient to inhibit the STAT protein.

The peptide or peptidomimetic can be administered to the cell by any method. For example, the peptide or peptidomimetic can be administered to a cell by contacting the cell with the peptide or peptidomimetic, typically in conjunction with a regent or other technique (e.g., microinjection or electroporation) that facilitates cellular uptake. Alternatively, and preferably, the peptide or peptidomimetic is administered by contacting the cell with a composition comprising the peptide or peptidomimetic and a cell penetrating motif, as discussed herein.

Alternatively, the peptide can be administered by introducing a nucleic acid encoding the amino acid sequence of the peptide into the cell such that the cell expresses a peptide comprising the amino acid sequence. The nucleic acid encoding the peptide can be introduced into the cell by any of various techniques, such as by contacting the cell with the nucleic acid or a composition comprising the nucleic acid as part of a construct, as described herein, that enables the delivery and expression of the nucleic acid. Specific protocols for introducing and expressing nucleic acids in cells are known in the art (see, e.g., Sambrook et al. (eds.), supra; and Ausubel et al., supra).

The peptide, peptidomimetic, or nucleic acid can be administered to a cell in vivo by administering the peptide, peptidomimetic, nucleic acid, or pharmaceutical composition comprising the peptide, peptidomimetic, or nucleic acid to a host comprising the cell. The host can be any host, such as a mammal, preferably a human. Suitable methods of administering peptides, peptidomimetics, and nucleic acids to hosts are known in the art, and discussed in greater detail in connection with the pharmaceutical composition, below.

The cell can be any type of cell that comprises a STAT protein. Preferably, the cell is of a type that overexpresses a STAT protein or is otherwise related to a disease or condition associated with STAT protein activity. For example, the cell can be an engineered cell that is designed to mimic a condition or disease associated with STAT activity, or the cell can be a cell of a patient afflicted with a disease or condition associated with STAT activity. Cancer cells are one example of a cell type that can be used. The cell can be in vitro or in vivo in any type of animal, such as a mammal, preferably a human.

The method of inhibiting a STAT protein in a cell can be used for any purpose, such as for the research, treatment, or prevention of diseases or conditions associated with STAT activity, particularly STAT overexpression. STAT overexpression, as the term is used herein, includes overproduction of STAT as well as aberrant activity (e.g., overactivity) of STAT for any reason (e.g., increased phosphorylation of STAT, mutations in the STAT protein, etc.). STAT overexpression has been linked to a large variety of cancers. Without wishing to be bound by any particular theory, it is believed that STAT is a necessary component of cancer cells, and that the administration of the peptide or peptidomimetic inhibits STAT thereby preventing the cancer cells from growing or surviving. Thus, according to one aspect of the method of inhibiting a STAT protein in a cell, the peptide or peptidomimetic is administered to a cancer cell, in vitro or in vivo, and administration of the peptide or peptidomimetic to the cancer cell inhibits the growth or survival of the cancer cell. In preferred embodiments of the invention, the peptide or peptidomimetic can be used to inhibit the growth or survival of the cancer cell without inhibiting the growth or survival of non-cancerous cells to any significant extent (e.g., without inhibiting the growth or survival of non-cancerous cells to an extent that would cause serious, undesirable side effects).

The cancer cell can be a cell of any type of cancer, in vitro or in vivo, particularly those associated with aberrant STAT activity. Non-limiting examples of specific types of cancers include cancer of the head and neck, eye, skin, mouth, throat, esophagus, chest, bone, lung, colon, sigmoid, rectum, stomach, prostate, breast, ovaries, kidney, liver, pancreas, brain, intestine, heart or adrenals. More particularly, cancers include solid tumor, sarcoma, carcinomas, fibrosarcoma, myxosarcoma, liposarcoma, chondrosarcoma, osteogenic sarcoma, chordoma, angiosarcoma, endotheliosarcoma, lymphangiosarcoma, lymphangioendothelio sarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, Kaposi's sarcoma, pinealoma, hemangioblastoma, acoustic neuroma, oligodendroglioma, menangioma, melanoma, neuroblastoma, retinoblastoma, a blood-born tumor, acute lymphoblastic leukemia, acute lymphoblastic B-cell leukemia, acute lymphoblastic T-cell leukemia, acute myeloblastic leukemia, acute promyelocytic leukemia, acute monoblastic leukemia, acute erythroleukemic leukemia, acute megakaryoblastic leukemia, acute myelomonocytic leukemia, acutenonlymphocytic leukemia, acute undifferentiated leukemia, chronic myelocytic leukemia, chronic lymphocytic leukemia, hairy cell leukemia, or multiple myeloma. See, e.g., Harrison's Principles of Internal Medicine, Eugene Braunwald et al., eds., pp. 491 762 (15th ed. 2001). The methods of the invention are believed to be especially useful for the treatment of blood malignancies and solid tumors, including lymphomas and leukemias, as well as breast, prostate, lung, head and neck, brain, and colon cancers.

STAT overexpression also has been linked to other diseases, including cardiovascular disease, inflammatory bowel disease, and ulcerative colitis, asthma, allergic reactions (believed to be associated with STAT6), and diabetes (believed to be associated with STAT4). Thus, the methods of the invention are believed to be useful for the treatment of such diseases as well.

The peptide also can be used, for example, to screen for other STAT inhibitors. Such a method can comprise, for instance, (a) combining a STAT protein, the peptide or peptidomimetic, and a test compound, (b) detecting binding of the STAT protein to the peptide or peptidomimetic in the presence of the test compound, and (c) comparing binding of the STAT protein to the peptide or peptidomimetic in the presence of the test compound to binding of the STAT protein to the peptide or peptidomimetic in the absence of the test compound, wherein a decrease in binding of the STAT protein to the peptide or peptidomimetic in the presence of the test compound as compared to such binding in the absence of the test compound indicates that the test compound is a STAT inhibitor candidate.

Also, the peptide or peptidomimetic can be used to screen for compounds that bind to the peptide or peptidomimetic, which compounds are likely to be STAT inhibitors. Various methods of detecting the binding of a compound to a peptide or peptidomimetic are known in the art. Such a method can comprise, for instance, (a) combining a test compound and the peptide or peptidomimetic, and (b) detecting binding of the test compound to the peptide or peptidomimetic, wherein binding of the test compound to the peptide or peptidomimetic indicates that the test compound is a STAT inhibitor candidate.

In accordance with the method of screening compounds, the test compound (or a library of test compounds) can be immobilized on a substrate, e.g., the surface of a well of a 96-well polystyrene microtiter plate, and the immobilized test compound(s) can be contacted with the peptide, peptidomimetic, or STAT protein as appropriate. Thereafter, the substrate is washed, and bound peptide, peptidomimetic, or STAT protein is detected. Alternatively, the peptide, peptidomimetic, or STAT protein, as appropriate, can be bound to the plate and subsequently contacted with one or more test compounds. Thereafter, the substrate can be washed, and bound test compounds detected. Specific protocols and methods for conducting such experiments, including contacting the compounds under suitable conditions, immobilizing compounds on a substrate, constructing libraries of test compounds, washing the substrate, and detecting bound compounds are well-known in the art.

Any one or more of the compounds or compositions of the invention described herein (e.g., peptide or peptidomimetic, nucleic acid, antibody, or cell) can be formulated as a pharmaceutical composition, comprising a compound of the invention and a pharmaceutically acceptable carrier. Furthermore, the compounds or compositions of the invention can be used in the methods described herein alone or as part of a pharmaceutical formulation.

The pharmaceutical composition can comprise more than one compound or composition of the invention. Alternatively, or in addition, the pharmaceutical composition can comprise one or more other pharmaceutically active agents or drugs. Examples of such other pharmaceutically active agents or drugs that may be suitable for use in the pharmaceutical composition include anticancer agents. Suitable anticancer agents include, without limitation, alkylating agents; nitrogen mustards; folate antagonists; purine antagonists; pyrimidine antagonists; spindle poisons; topoisomerase inhibitors; apoptosis inducing agents; angiogenesis inhibitors; podophyllotoxins; nitrosoureas; cisplatin; carboplatin; interferon; asparaginase; tamoxifen; leuprolide; flutamide; megestrol; mitomycin; bleomycin; doxorubicin; irinotecan; and taxol, geldanamycin (e.g., 17-AAG), and various anti-cancer peptides and antibodies.

The carrier can be any of those conventionally used and is limited only by physiochemical considerations, such as solubility and lack of reactivity with the active compound(s), and by the route of administration. The pharmaceutically acceptable carriers described herein, for example, vehicles, adjuvants, excipients, and diluents, are well-known to those skilled in the art and are readily available to the public. It is preferred that the pharmaceutically acceptable carrier be one which is chemically inert to the active agent(s) and one which has no detrimental side effects or toxicity under the conditions of use.

The choice of carrier will be determined in part by the particular compound or composition of the invention and other active agents or drugs used, as well as by the particular method used to administer the compound and/or inhibitor. Accordingly, there are a variety of suitable formulations of the pharmaceutical composition of the present inventive methods. The following formulations for oral, aerosol, parenteral, subcutaneous, intravenous, intramuscular, interperitoneal, rectal, and vaginal administration are exemplary and are in no way limiting. One skilled in the art will appreciate that these routes of administering the compound of the invention are known, and, although more than one route can be used to administer a particular compound, a particular route can provide a more immediate and more effective response than another route.

Injectable formulations are among those formulations that are preferred in accordance with the present invention. The requirements for effective pharmaceutical carriers for injectable compositions are well-known to those of ordinary skill in the art (See, e.g., Pharmaceutics and Pharmacy Practice, J.B. Lippincott Company, Philadelphia, Pa., Banker and Chalmers, eds., pages 238-250 (1982), and ASHP Handbook on Injectable Drugs, Toissel, 4th ed., pages 622-630 (1986)).

Topical formulations are well-known to those of skill in the art. Such formulations are particularly suitable in the context of the present invention for application to the skin.

Formulations suitable for oral administration can consist of (a) liquid solutions, such as an effective amount of the inhibitor dissolved in diluents, such as water, saline, or orange juice; (b) capsules, sachets, tablets, lozenges, and troches, each containing a predetermined amount of the active ingredient, as solids or granules; (c) powders; (d) suspensions in an appropriate liquid; and (e) suitable emulsions. Liquid formulations may include diluents, such as water and alcohols, for example, ethanol, benzyl alcohol, and the polyethylene alcohols, either with or without the addition of a pharmaceutically acceptable surfactant. Capsule forms can be of the ordinary hard- or soft-shelled gelatin type containing, for example, surfactants, lubricants, and inert fillers, such as lactose, sucrose, calcium phosphate, and corn starch. Tablet forms can include one or more of lactose, sucrose, mannitol, corn starch, potato starch, alginic acid, microcrystalline cellulose, acacia, gelatin, guar gum, colloidal silicon dioxide, croscarmellose sodium, talc, magnesium stearate, calcium stearate, zinc stearate, stearic acid, and other excipients, colorants, diluents, buffering agents, disintegrating agents, moistening agents, preservatives, flavoring agents, and pharmacologically compatible excipients. Lozenge forms can comprise the active ingredient in a flavor, usually sucrose and acacia or tragacanth, as well as pastilles comprising the active ingredient in an inert base, such as gelatin and glycerin, or sucrose and acacia, emulsions, gels, and the like containing, in addition to the active ingredient, such excipients as are known in the art.

The compounds and compositions of the invention, alone or in combination with other suitable components, can be made into aerosol formulations to be administered via inhalation. These aerosol formulations can be placed into pressurized acceptable propellants, such as dichlorodifluoromethane, propane, nitrogen, and the like. They also may be formulated as pharmaceuticals for non-pressured preparations, such as in a nebulizer or an atomizer. Such spray formulations also may be used to spray mucosa.

Formulations suitable for parenteral administration include aqueous and non-aqueous, isotonic sterile injection solutions, which can contain anti-oxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. The compounds and compositions of the invention can be administered in a physiologically acceptable diluent in a pharmaceutical carrier, such as a sterile liquid or mixture of liquids, including water, saline, aqueous dextrose and related sugar solutions, an alcohol, such as ethanol, isopropanol, or hexadecyl alcohol, glycols, such as propylene glycol or polyethylene glycol, dimethylsulfoxide, glycerol ketals, such as 2,2-dimethyl-1,3-dioxolane-4-methanol, ethers, such as poly(ethyleneglycol) 400, an oil, a fatty acid, a fatty acid ester or glyceride, or an acetylated fatty acid glyceride with or without the addition of a pharmaceutically acceptable surfactant, such as a soap or a detergent, suspending agent, such as pectin, carbomers, methylcellulose, hydroxypropylmethylcellulose, or carboxymethylcellulose, or emulsifying agents and other pharmaceutical adjuvants.

Oils, which can be used in parenteral formulations include petroleum, animal, vegetable, or synthetic oils. Specific examples of oils include peanut, soybean, sesame, cottonseed, corn, olive, petrolatum, and mineral. Suitable fatty acids for use in parenteral formulations include oleic acid, stearic acid, and isostearic acid. Ethyl oleate and isopropyl myristate are examples of suitable fatty acid esters.

Suitable soaps for use in parenteral formulations include fatty alkali metal, ammonium, and triethanolamine salts, and suitable detergents include (a) cationic detergents such as, for example, dimethyl dialkyl ammonium halides, and alkyl pyridinium halides, (b) anionic detergents such as, for example, alkyl, aryl, and olefin sulfonates, alkyl, olefin, ether, and monoglyceride sulfates, and sulfosuccinates, (c) nonionic detergents such as, for example, fatty amine oxides, fatty acid alkanolamides, and polyoxyethylenepolypropylene copolymers, (d) amphoteric detergents such as, for example, alkyl-b-aminopropionates, and 2-alkyl-imidazoline quaternary ammonium salts, and (e) mixtures thereof.

Preservatives and buffers may be used. In order to minimize or eliminate irritation at the site of injection, such compositions may contain one or more nonionic surfactants having a hydrophile-lipophile balance (HLB) of from about 12 to about 17. The quantity of surfactant in such formulations will typically range from about 5% to about 15% by weight. Suitable surfactants include polyethylene sorbitan fatty acid esters, such as sorbitan monooleate and the high molecular weight adducts of ethylene oxide with a hydrophobic base, formed by the condensation of propylene oxide with propylene glycol. The parenteral formulations can be presented in unit-dose or multi-dose sealed containers, such as ampoules and vials, and can be stored in a freeze-dried (lyophilized) condition requiring only the addition of the sterile liquid excipient, for example, water, for injections, immediately prior to use. Extemporaneous injection solutions and suspensions can be prepared from sterile powders, granules, and tablets of the kind previously described.

Additionally, the compounds of the invention, or compositions comprising such compounds, can be made into suppositories by mixing with a variety of bases, such as emulsifying bases or water-soluble bases. Formulations suitable for vaginal administration can be presented as pessaries, tampons, creams, gels, pastes, foams, or spray formulas containing, in addition to the active ingredient, such carriers as are known in the art to be appropriate.

The following examples further illustrate the invention but, of course, should not be construed as in any way limiting its scope.

EXAMPLES

Except as otherwise stated, the peptides referenced in the following examples were prepared using one of the following general procedures:

Peptide Synthesis.

The peptides were synthesized by solid phase peptide synthesis on a peptide synthesizer equipped with a conductivity monitoring unit utilizing Fmoc amino acid derivatives. The synthesis was performed with conditional blocking of un-reacted amino groups with acetic anhydride for easier purification of the resulting peptides. During the synthesis of the peptides with C-terminal Cys, deprotection was performed with 20% piperidine containing 0.1 M HOBt to avoid the formation of dehydro-alanine. The synthesizer was reprogrammed to deliver appropriate amounts of deprotection mixture composed of 0.25 M HOBt in 50% piperidine in N-methyl-pyrrolidone. Peptides were cleaved from the resin with 87.5% trifluoroacetic acid containing 5% water, 5% thioanisol and 2.5% triisopropyl-silane (v/v), precipitated with cold diethyl ether, washed five times with ether, and dried in vacuum overnight. Peptides dissolved in dimethylformamide were purified by HPLC on a preparative (25×250 mm) C18 reverse phase column in a gradient of 0.05% (v/v) trifluoroacetic acid in water and acetonitrile containing 0.05% trifluoroacetic acid. The fractions were analyzed by electrospray LC/MS with the use of a Zorbax 300SB-C18 Poroshell column and a gradient of 5% acetic acid in water and acetonitrile. Only fractions containing more than 95% pure product were combined and freeze-dried. Peptides were dried from 5% acetic acid to ensure conversion into acetate salts. The purity and structure were further confirmed by LC/MS with separation in a Zorbax 300SB-C18 analytical column and Microsorb-MW 300A C8 column.

Synthesis of Cyclic Peptides.

The linear peptide precursors were synthesized on an peptide synthesizer using Fmoc chemistry and starting with Rink Amide resin. After completion of peptide elongation, the Mmt protecting group on Lys was removed by treating with 1% TFA in DCM to afford the resin bound peptide. The resin-bound protected peptide was N-terminally bromoacetylated by three equivalents of bromoacetic anhydride in DMF at room temperature overnight. Then the peptide was cleaved from the resin by using TFA containing 2.5% each (v/v) of triethylsilane and deionized water (2 h). For isolation of the product, two-thirds of the cleavage reagent mixture was evaporated under N2 stream and the residue was triturated and washed with ice-cold ether. The precipitated crude peptide was dissolved in 50 mL of water and added dropwise into 100 mL of aqueous solution, which was adjusted to pH 8-9 with 0.2M aqueous solution of NH4OH and NH4OAc (1:1, mol/mol), repeatedly. After 6 h stirring at room temperature, the cyclization reaction was quenched by addition of 30% acetic acid. Peptides were purified by preparative RP HPLC as described above.

Example 1

This example demonstrates the growth inhibitory and cell-killing activity of a peptide of the invention.

NMR studies suggest that the N-terminal domain of STAT4 is formed by two helices: a 12-residue helix 2 and a 20-residue helix 8. The corresponding helices derived from STAT3 were synthesized and each was fused to the N-terminus of penetratin. MCF-7 breast cancer cells were treated with either the helix-2 or helix-8 derivative. Table 4 shows the number of cells remaining in each culture after treatment as a percentage of the cells remaining in an untreated culture.

As demonstrated by the results shown in Table 4, the penetratin derivative of helix 2 showed much higher growth inhibition and cell-killing activity as compared to the penetratin derivative of helix 8 when tested on MCF-7 breast cancer cells.

TABLE 4

| Concentration (μM) | Cell Number, % of Untreated Cells | |
|---|---|---|
| | Helix 8-Penetrin Derivative | Helix 2-Penetrin Derivative |
| 0 | 100 | 100 |
| 1 | 100 | 58 |
| 5 | 100 | 39 |
| 10 | 67 | −100 |

Example 2

This example demonstrates the use of peptides or peptidomimetics of the invention to inhibit the growth or survival of cancer cells.

A library of synthetic peptide analogs of STAT3 helix 2 was constructed, and the growth inhibitory activity of each peptide was tested in MCF7 breast cancer cells. To enable cell membrane penetration, penetratin (RQIKIWFPNRR-Nle-KWKK-NH$_2$ (SEQ ID NO: 74)) was fused to the C-termini of all peptides. The sequences of the peptides are presented in Table 5, wherein amino acid substitutions in the native sequences are underlined.

Activity was determined by MTT assay 48 hours after exposure of the MCF7 cells to the test compounds. Many of the derivatives exhibited significant cell killing activity at 10 μM, creating steep activity curves and introducing significant errors in determining IC$_{50}$ values. For this reason, activity at 5 μM was used as criteria for comparison instead of IC$_{50}$ values. The results are presented in Table 5.

As the results show, all peptides demonstrated some level of growth inhibition. The most significant improvements in potency were achieved by substituting the Gln 20 residue with Lys (Hel2A) or diaminobutyric acid (Dab) (Hel2H, Hel2I and Hel2K), or by substituting Ser23 with Arg or Lys (Hel2A-2). The peptide corresponding to a fusion of helixes one and two (Hel2G) was less active than peptides comprising only helix 2 or a derivative thereof without helix 8.

The results indicate that the peptides can be used to inhibit STAT and slow or inhibit cell growth and survival.

TABLE 5

| Peptide Identifier | SEQ ID NO | Sequence | Cell growth, % of control |
|---|---|---|---|
| Hel2-Pen | 12 | LDTRYLEQLHQLYS | 73 ± 5 |
| Hel2A-Pen | 13 | DTRYLEQLHKLYS | 44 ± 5 |
| Hel2B-Pen | 14 | LDTRYLEQLHKLYS | 82 ± 6 |
| Hel2C-Pen | 15 | DTRYLEQLHKLCyPheS | 38 ± 4 |
| Hel2D-Pen | 16 | DTKYLEQLHKLYS | 42 ± 4 |
| Hel2E-Pen | 17 | DTRYLQELHKLYS | 46 ± 4 |
| Hel2F-Pen | 18 | DTRYLEQLHDabLYS | 60 ± 5 |
| Hel2G-Pen | 19 | AQWNQLQQLDTRYLEQLHQLYS | 80 ± 5 |
| Hel2A-2-Pen | 20 | LDTRYLEQLHKLY | 65 ± 4 |
| Hel2A-2a-Pen | 21 | DTRYLEQLHKLY | 65 ± 5 |
| Ac-Hel2A-2a-Pen | 22 | Ac-DTRYLEQLHKLY | 45 ± 5 |
| Hel2H-Pen | 23 | LDTRYLEQLHDabLY | 45 ± 4 |
| Hel2I-Pen | 24 | DTRYLEQLHDabLY | 25 ± 4 |
| Hel2K-Pen | 25 | LDTKYLEQLHDabLY | 8 ± 2 |
| Hel2A-3-Pen | 26 | Ac-DTRYLEQLHALY | 93 ± 6 |
| Hel2A-4-Pen | 27 | Ac-DTRYLEQLHELY | 91 ± 6 |
| Hel2A-5-Pen | 28 | Ac-ATRYLEQLHKLY | 85 ± 5 |

*CyPhe refers to 4-cyano phenylalanine

Example 3

This example demonstrates the use of peptides or peptidomimetics of the invention to inhibit STAT-activated transcription.

Selected peptides were tested for inhibition of STAT3 signaling in breast cancer cell lines by luciferase reporter assay. The assay employed the Mercury JAK-STAT Pathway Profiling system (Clontech), which includes the enhancer elements GAS (interferon-γ activating sequence) or STAT3 (a modified GAS sequence) introduced as three tandem copies upstream of the TA promoter in a luciferase reporter vector. STAT3 helix 2 analogs reduced basal expression of the reporter construct containing the GAS, or STAT3 elements in MCF-7 cells within one hour after treatment. Luciferase vector with no insertion upstream of the TA promoter served as a negative control and showed no change in luciferase activity upon treatment. The results are presented in Table 6.

The assays identified STAT3 Hel2A-2 peptide as the most potent derivative. These results demonstrate that the peptides and peptidomimetic compounds of the invention can be used to inhibit STAT activity.

TABLE 6

| Peptide Identifier | SEQ ID NO | Sequence | Activity, % of control |
|---|---|---|---|
| Hel2-Pen | 12 | LDTRYLEQLHQLYS | 56 ± 5 |
| Hel2A-pen | 13 | DTRYLEQLHKLYS | 100 ± 9 |
| Hel2B-Pen | 14 | LDTRYLEQLHKLYS | 100 ± 9 |
| Hel2A-2-Pen | 20 | LDTRYLEQLHKLY | 71 ± 6 |
| Hel2H-Pen | 23 | LDTRYLEQLHDabLY | 43 ± 4 |
| Hel2I-Pen | 24 | DTRYLEQLHDabLY | 53 ± 6 |
| Hel2A-3-Pen | 26 | Ac-DTRYLEQLHALY | 89 ± 9 |

Example 4

This example demonstrates the use of peptides or peptidomimetics of the invention to inhibit the growth or survival of cancer cells.

Peptides were constructed based on variations of the amino acid sequence of the second helix of STAT1 and STAT5a. ε-palmitoyl lysine was substituted for penetratin as a cell-penetrating motif Several residues of penetratin sequence were preserved in the lipopeptide derivatives, which served as a linking sequence. The peptides and peptidomimetics were tested for growth inhibitory and cytotoxic activity in MCF7 cells using an MTT assay as described in Example 2. The results are presented in Table 7, wherein $IC_{50}$ is the concentration of inhibitor causing 50% growth inhibition.

TABLE 7

| Peptide | SEQ ID NO | Sequence | $IC_{50}$ (μM). |
|---|---|---|---|
| ST1-H2-K-Pal | 55 | DSKFLEQVHKLYRQIK-ε-Pal | >10 |
| ST1-H2-Pal1 | 58 | Pal-IQRYLKHVQELFKSD (all-D) | 0.8 |
| ST1-H2-Pal2 | 59 | Pal-IQKYLKHVQELFKSD (all-D) | 0.65 |
| ST5-H2a-K-Pal | 65 | LQGDALRQ-Nle-QVLYRQIK-ε-Pal | 0.45 |
| ST5-H2-3-K-Pal | 63 | QGDALRQ-Nle-QVLYRQIK-ε-Pal | 0.6 |
| ST3-H2a-K-Pal | 30 | DTKYLEQLHKLYKK-ε-Pal | 1.05 |
| ST3-H2a-K-Pal-Cyc1 | 32 | DTKYCEQLKKLYKK-ε-Pal | 1.05 |
| ST3-H2a-K-Pal-Cyc2 | 34 | DTKCLEQKHKLYKK-ε-Pal | 1.35 |

As shown by the results in Table 7, the STAT5 derivatives showed significant growth inhibitory activity in breast cancer cells; however, the STAT1 derivative was not active in this assay. Retroinverso analogues of the peptides, which comprised inverse sequences and all D-amino acids, also were prepared and tested. The retroinverso analogues were as active as the corresponding L-amino acid peptides in case of STAT3 (data not shown), while the retroinverso analogue of STAT1 exhibited significantly enhanced cytotoxicity as compared to the corresponding L-amino acid peptide.

Example 5

This example demonstrates the use of peptides or peptidomimetics of the invention to inhibit the growth or survival of cancer cells.

Retro-inverso peptide analogues were prepared comprising variants of the sequence of helix 2 of STAT3. STAT3-Hel2A-2 (see Example 3) was used as a starting sequence, in which all but three residues of the original penetratin sequence was replaced with palmitic acid. The variants were produced by systematically truncating and substituting the base sequence. The compounds were used to treat MCF7 breast cancer cells. $IC_{50}$ values were determined 48 hours after exposing the cells to the test compounds. The results are presented in Table 8, wherein $IC_{50}$ is the concentration of inhibitor causing 50% growth inhibition.

TABLE 8

| Peptide | Sequence ID No. | Sequence | IC$_{50}$, µM. |
|---|---|---|---|
| St3-H2a-2a-Pal1 | 40 | Pal-IQRYLKHLQELYRTD (all-D) | 2.6 |
| St3-H2a-2a-Pal2 | 41 | Pal-IQKYLKHLQELYRTD (all-D) | 2.1 |
| St3-H2a-2a-Pal3 | 42 | Pal-QRYLKHLQELYRTD (all-D) | 2.3 |
| St3-H2a-2a-Pal4 | 43 | Pal-RYLKHLQELYRTD (all-D) | 3.5 |
| St3-H2a-2a-Pal6 | 44 | Pal-QKYLKHLQELYRTD (all-D) | 4.1 |
| St3-H2a-2a-Pal7 | 45 | Pal-KYLKHLQELYRTD (all-D) | 1.8 |
| St3-H2a-2a-Pal8 | 47 | Pal-IQRYLKHLQQLYRTD (all-D) | 3.1 |
| St3-H2a-2a-Pal9 | 49 | Pal-IQRYLKHLQQLYRTN (all-D) | 1.7 |
| St3-H2a-2a-Pal10 | 50 | Pal-YLKHLQELYRTD (all-D) | 3.5 |
| St3-H2a-2a-Pal11 | 51 | Pal-QRYLKHLQELYRTDL (all-D) | 2.7 |
| St3-H2a-2a-Pal12 | 52 | Pal-YLKHLQQLYRTN (all-D) | >10 |

Two N-terminal residues of the original sequence (Ile and Gln) could be eliminated without much change in activity. The presence of a positively charged residue on the N-terminus of the inverted peptide appeared to enhance activity (ST3-H2a-2a-Pal10 and ST3-H2a-2a-Pal12). C-terminal Asp could be substituted with Asn (ST3-H2a-2a-Pal9) with some gain in activity. Glu also could be replaced with Gln, but with some loss in potency (ST3-H2a-2a-Pal8). ST3-H2a-2a-Pal7 comprising only 13 residues was a potent inhibitor with an IC$_{50}$ of 1.8 µM.

Example 6

The following example illustrates that peptides and peptidomimetics of the invention interact with STAT proteins in living cells.

Fluorescence Resonance Energy Transfer (FRET) method was used to determine whether STAT3-HEL2A-2 (see Example 3) interacts with STAT3 in living cells. HEK293 cells stably expressing STAT3 tagged with eGFP on its N-terminus (eGFP-STAT3) were treated for one hour with 5 µM of STAT3-HEL2A-2 labeled with rhodamine. An additional cysteine residue was positioned at the C-terminus of penetratin to facilitate labeling. Excitation of eGFP (donor) was facilitated using a 488-nm light source, and the emission spectrum was detected. In the absence of energy transfer between eGFP and rhodamine, excitation of eGFP would lead to an emission peak at 520-540 nm, whereas energy transfer from eGFP to an adjacent rhodamine fluorochrome acceptor would cause an emission in the 560-600 nm range. It was found that treatment with rhodamine-labeled STAT3-HEL2A-2 quenched the normal fluorescence of eGFP by 90%. To confirm that FRET was occurring, acceptor photobleaching was performed with a 561 nm laser using an LSM 510 confocal microscope (Zeiss). The photobleaching of rhodamine restored the fluorescence of eGFP. These results show that STAT3-HEL2A-2 interacts with STAT3 in living cells.

Example 7

The following example demonstrates that a peptide or peptidomimetic comprising a variant of helix 2 of STAT3 interacts specifically with STAT3 in living cells.

Cells expressing eGFP-STAT3, eGFP-STAT1, or eGFP were treated with rhodamine-labeled STAT3-HEL2A-2 (see Example 6). Excitation of eGFP was facilitated, and the emission spectrum detected, in accordance with the methods described in Example 6. FRET efficiency was calculated using equation 1-D0/D1, where D0 is fluorescence intensity of eGFP before rhodamine photobleaching and D1 is the intensity after rhodamine photobleaching.

It was found that STAT3-HEL2A-2 interacted very efficiently with STAT3 (90.8%), whereas binding to STAT1 and eGFP was equally inefficient (approximately 12.8% and 15.2%, respectively). Thus, FRET analysis demonstrates that STAT3-HEL2A-2 interacts specifically and efficiently with STAT3 in living cells.

Example 8

The following example demonstrates the specificity of STAT-based inhibitors.

MCF-7 and MDA-MB-231 cells were treated with Leukemia Inhibitory Factor (LIF) to activate STAT3 and with Interferon gamma (IFN-γ) to activate STAT1 signaling. In MCF-7 cells, LIF induced selective STAT3 tyrosine phosphorylation and IFN-γ induced selective STAT1 tyrosine phosphorylation. In MDA-MB-231 cells, however, each cytokine induced both STAT3 and STAT1 tyrosine phosphorylation.

Pretreatment of the cells with STAT3-Hel2A-2 (SEQ ID NO: 20; Example 2) or STAT1-Hel2A-2 (DSKFLEQVH-KLY-penetratin; (SEQ ID NO: 76)) for 1 hour did not affect tyrosine phosphorylation of STAT3 and STAT1, and the inhibitors did not change expression levels of STAT3 and STAT1 proteins. These data support earlier findings that the STAT3 N-domain is not required for tyrosine phosphorylation (Zhang et al., Mol. Cell. Biochem. 288, 179-189 (2006)).

To evaluate effects of inhibitors on cytokine-activated transcription, luciferase reporter vectors APRE and ISRE were employed (Takeda et al., J. Endocrinol. 159, 323-330 (1998); Ivanova et al., J. Mol. Biol. 340, 641-653 (2004)). APRE was activated in MCF-7 cells by LIF. STAT3-Hel2A-2 and STAT1-Hel2A-2 inhibited both basal and stimulated expression. The ISRE reporter, containing three tandem copies of STAT1-STAT2 dimers DNA binding sites, was activated in MCF-7 cells by IFN-γ, and only the STAT1-Hel2A-2 inhibitor prevented cytokine-stimulated reporter activation.

Taken together, these data demonstrate that the STAT3-Hel2A-2 inhibitor specifically inhibits STAT3-dependent transcription, but not STAT1-dependent transcription, without affecting the levels of STAT3 protein expression or STAT3 tyrosine phosphorylation.

Example 9

The following example further demonstrates the use of the peptides and peptidomimetics of the invention to inhibit cancer cells.

Three breast cancer cell lines (MDA-MB-231, T47D, and MDA-MB-435) and normal breast epithelial (MCF-10A) were treated with escalating doses of STAT3-Hel2A-2 (SEQ ID NO: 20). Cell proliferation and cell death were estimated by MTT assay.

The STAT3-based inhibitor induced death of MDA-MB-231 and MDA-MB-435 breast cancer cells, and inhibited proliferation of T47D cells, in a dose-dependent manner. Lower sensitivity of MCF-7 and T47D cells compared to MDA-MB-231 and MDA-MB-435 cells correlates well with the level of basal STAT3 activation. MCF-7 and T47D cells have a low level of activated STAT3, whereas MDA-MB-231 and MDA-MB-435 have elevated levels of tyrosine 705-phosphorylated STAT3. The fact that survival of MCF-7 and T47D cells is also affected by inhibition of STAT3 is in agreement with previously published observation that even unphosphorylated STAT3 has an important role in oncogenesis and might be a promising target for tumor therapy (Yang et al., Cancer Res. 65, 939-947 (2005)).

In addition, growth and viability of normal mammary epithelial cells MCF-10A were not altered significantly. Furthermore, survival of normal mouse embryonic fibroblasts (MEFs) and STAT3-deficient MEFs was not affected by treatment with STAT3-Hel2A-2 (data not shown). Our data along with published reports (Schlessinger et al. Cancer Res. 65, 5828-5834 (2005)) show that survival of many tumor-derived cell lines depends on the activity of STAT3, whereas normal cells are perfectly viable without STAT3. This observation potentially provides a basis for an enhanced therapeutic ratio, based on differential inhibitor effects

Example 10

The following example further demonstrates the use of the peptides and peptidomimetics of the invention to inhibit cancer cells.

Human breast carcinoma cell lines MDA-MB-231 and MCF-7 were treated with STAT3-Hel2A-2 (SEQ ID NO: 20) or 0.05% DMSO as a control for 2 hours and analyzed by annexin V binding and flow cytometry. At 5 µM, STAT3-Hel2A-2 induced significant increase in Annexin V binding in both cell lines in 2 hours. Morphological changes in the cells could be observed within minutes after addition of the peptides conjugated to penetratin. Dose-response curves showed sharp increase in activity over a small range of concentration. Lack of gradual increase in activity may be due to high concentration of the target protein. It was shown that STAT3 is expressed in human T-cells (Jurkat cells) at levels that are about hundred-fold higher than STAT1 or HIF-1α (Phillips et al., Biomed. Chromatogr. 17, 182-187 (2003)). The reported levels of 100-200 pg/100 cells are equivalent to intracellular concentrations of at least 5-10 µM. Thus, the observed concentration-dependence toxicity curves may be reflecting the titration of a protein that is present in significant quantities.

To confirm apoptotic mechanism of cell death, in-situ measurement of mitochondrial membrane potential ($\Delta\Psi$) was performed using a MitoTracker™ Red CMXRos (Invitrogen Corp., Carlsbad, Calif.), a red-fluorescent dye that stains mitochondria in live cells. Its accumulation is dependent upon membrane potential. Treatment with STAT3-Hel2A-2 caused more than 50% of the MDA-MB-231 and MCF-7 cells to decrease mitochondrial membrane potential, which leads to apoptosis.

The degree of Poly (ADP-ribose) polymerase (PARP) cleavage, a marker of caspase-dependent apoptosis, also was analyzed. MCF-7 cells are caspase-3 deficient, and for this reason we could not evaluate PARP cleavage in this cell line. In MDA-MB-231 cells, however, significant PARP cleavage was detected after 8 hours of treatment with STAT3-Hel2A-2. Although STAT1 and STAT5b inhibitors decreased survival of breast cancer cells with almost the same efficiency as STAT3 derivatives, they had little, if any, effect on PARP cleavage and mitochondrial membrane potential.

The observed effects of STAT3 inhibition on mitochondrial function are in agreement with described STAT3 localization in mitochondria and its essential role in the function of these organelles. Toxicity of STAT1 and STAT5b helix 2 analogs is in agreement with previously observed induction of apoptosis in breast cancer cells by down regulation of STAT1 and STAT5b. STAT4 helix 2 derivatives were non-toxic for breast cancer cells.

Taken together, these results demonstrate that STAT3-Hel2A is effective in inducing apoptosis in breast cancer cells, probably through changes in the mitochondrial membrane potential that result in activation of caspases.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. An isolated peptide or peptidomimetic of 40 or fewer amino acids in length that binds to a STAT protein, wherein the peptide or peptidomimetic comprises at least one of:
   (a) the amino acid sequence of any of SEQ ID NOs: 32-34 or reverse thereof, wherein the amino acid sequence optionally is cyclized;
   (b) the amino acid sequence of Tyr Leu Xaa4 Gln Xaa3 Gln Xaa2 Leu Ala Xaa1 Gly Gln (SEQ ID NO: 66), wherein
      (i) Xaa1 is Asp or Glu,
      (ii) Xaa2 is Arg, His, or Lys,
      (iii) Xaa3 is norleucine (Nle) or Met, and
      (iv) Xaa4 is Val or Ala; or
   (c) the amino acid sequence of any of SEQ ID NOs: 11 or 38.

2. The peptide or peptidomimetic of claim 1, wherein the peptide or peptidomimetic comprises the amino acid sequence of SEQ ID NO: 11 or the reverse sequence thereof (SEQ ID NO: 38).

3. The peptide or peptidomimetic of claim 1, wherein the peptide or peptidomimetic comprises the amino acid sequence of any of SEQ ID NOs: 32-34, wherein the amino acid sequence optionally is cyclized.

4. The peptide or peptidomimetic of claim 1, wherein the peptide or peptidomimetic comprises the amino acid sequence of Tyr Leu Xaa4 Gln Xaa3 Gln Xaa2 Leu Ala Xaa1 Gly Gln (SEQ ID NO: 66), wherein
   (i) Xaa1 is Asp or Glu,
   (ii) Xaa2 is Arg, His, or Lys,
   (iii) Xaa3 is norleucine (Nle) or Met, and
   (iv) Xaa4 is Val or Ala.

5. The peptide or peptidomimetic of claim 1, wherein the amino acids are D-amino acids.

6. The peptide or peptidomimetic of claim 1 further comprising a cell-penetrating motif.

7. The peptide or peptidomimetic of claim 6, wherein the cell-penetrating motif is a protein transduction domain or fatty acid, optionally attached to the peptide or peptidomimetic via a linker sequence.

8. The peptide or peptidomimetic of claim 1, wherein the peptide or peptidomimetic comprises a terminal acetyl or palmitoyl group.

9. The peptide or peptidomimetic of claim 8, wherein the peptide or peptidomimetic comprises a terminal ε-palmitoyl modified lysine residue.

10. The peptide of peptidomimetic of claim 1, wherein the peptide or peptidomimetic binds the N-terminal domain of a STAT protein.

11. A pharmaceutical composition comprising the peptide or peptidomimetic of claim 1 and a pharmaceutically acceptable carrier.

12. The pharmaceutical composition of claim 11, further comprising one or more active agents or drugs.

13. The peptide or peptidomimetic of claim 3, wherein the amino acid sequence is cyclized by the interaction of:
   (i) the cysteine residue at position 5 and the lysine residue at position 9 of SEQ ID NO: 32,
   (ii) the cysteine residue at position 4 and the lysine residue at position 8 of SEQ ID NO: 33, or
   (iii) the cysteine residue at position 4 and the lysine residue at position 8 of SEQ ID NO: 34.

14. An isolated peptide or peptidomimetic of 40 or fewer amino acids in length that binds to a STAT protein, wherein the peptide or peptidomimetic comprises at least one of:
   (a) the amino acid sequence of any of SEQ ID NOs: 32-34 or retro-inverso version thereof;
   (b) the amino acid sequence of Tyr Leu Xaa4 Gln Xaa3 Gln Xaa2 Leu Ala Xaa1 Gly Gln (SEQ ID NO: 66) or inverse thereof, wherein
      (iii) Xaa1 is Asp or Glu,
      (iv) Xaa2 is Arg, His, or Lys,
      (iii) Xaa3 is norleucine (Nle) or Met, and
      (iv) Xaa4 is Val or Ala; or
   (c) the amino acid sequence of SEQ ID NO: 11 or retro-inverso version thereof.

* * * * *

```
                           SEQUENCE LISTING

<160> NUMBER OF SEQ ID NOS: 80

<210> SEQ ID NO 1
  <211> LENGTH: 45
  <212> TYPE: PRT
  <213> ORGANISM: Homo sapiens

<400> SEQUENCE: 1

Met Ser Gln Trp Tyr Glu Leu Gln Gln Leu Asp Ser Lys Phe Leu Glu
  1               5                   10                  15

Gln Val His Gln Leu Tyr Asp Asp Ser Phe Pro Met Glu Ile Arg Gln
              20                  25                  30

Tyr Leu Ala Gln Trp Leu Glu Lys Gln Asp Trp Glu His
          35                  40                  45

<210> SEQ ID NO 2
  <211> LENGTH: 45
  <212> TYPE: PRT
  <213> ORGANISM: Homo sapiens

<400> SEQUENCE: 2

Met Ala Gln Trp Glu Met Leu Gln Asn Leu Asp Ser Pro Phe Gln Asp
  1               5                   10                  15

Gln Leu His Gln Leu Tyr Ser His Ser Leu Leu Pro Val Asp Ile Arg
              20                  25                  30

Gln Tyr Leu Ala Val Trp Ile Glu Asp Gln Asn Trp Gln
          35                  40                  45

<210> SEQ ID NO 3
  <211> LENGTH: 45
  <212> TYPE: PRT
  <213> ORGANISM: Homo sapiens

<400> SEQUENCE: 3

Met Ala Gln Trp Asn Gln Leu Gln Gln Leu Asp Thr Arg Tyr Leu Glu
  1               5                   10                  15

Gln Leu His Gln Leu Tyr Ser Asp Ser Phe Pro Met Glu Leu Arg Gln
              20                  25                  30

Phe Leu Ala Pro Trp Ile Glu Ser Gln Asp Trp Ala Tyr
          35                  40                  45

<210> SEQ ID NO 4
  <211> LENGTH: 45
  <212> TYPE: PRT
  <213> ORGANISM: Homo sapiens

<400> SEQUENCE: 4

Met Ser Gln Trp Asn Gln Val Gln Gln Leu Glu Ile Lys Phe Leu Glu
  1               5                   10                  15

Gln Val Asp Gln Phe Tyr Asp Asp Asn Phe Pro Met Glu Ile Arg His
              20                  25                  30

Leu Leu Ala Gln Trp Ile Glu Asn Gln Asp Trp Glu Ala
          35                  40                  45

<210> SEQ ID NO 5
```

```
<211> LENGTH: 45
<212> TYPE: PRT
<213> ORGANISM: Homo sapiens

<400> SEQUENCE: 5

Met Ala Gly Trp Ile Gln Ala Gln Gln Leu Gln Gly Asp Ala Leu Arg
1               5                   10                  15

Gln Met Gln Val Leu Tyr Gly Gln His Phe Pro Ile Glu Val Arg His
                20                  25                  30

Tyr Leu Ala Gln Trp Ile Glu Ser Gln Pro Trp Asp Ala
        35                  40                  45

<210> SEQ ID NO 6
<211> LENGTH: 45
<212> TYPE: PRT
<213> ORGANISM: Homo sapiens

<400> SEQUENCE: 6

Met Ala Val Trp Ile Gln Ala Gln Gln Leu Gln Gly Glu Ala Leu His
1               5                   10                  15

Gln Met Gln Ala Leu Tyr Gly Gln His Phe Pro Ile Glu Val Arg His
                20                  25                  30

Tyr Leu Ser Gln Trp Ile Glu Ser Gln Ala Trp Asp Ser
        35                  40                  45

<210> SEQ ID NO 7
<211> LENGTH: 45
<212> TYPE: PRT
<213> ORGANISM: Homo sapiens

<400> SEQUENCE: 7

Met Ser Leu Trp Gly Leu Val Ser Lys Met Pro Pro Glu Lys Val Gln
1               5                   10                  15

Arg Leu Tyr Val Asp Phe Pro Gln His Leu Arg His Leu Leu Gly Asp
                20                  25                  30

Trp Leu Glu Ser Gln Pro Trp Glu Phe Leu Val Gly Ser
        35                  40                  45

<210> SEQ ID NO 8
<211> LENGTH: 12
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Xaa can be any amino acid
<220> FEATURE:
<221> NAME/KEY: MISC_FEATURE
<222> LOCATION: (3)..(3)
<223> OTHER INFORMATION: Xaa can be any amino acid
<220> FEATURE:
<221> NAME/KEY: MISC_FEATURE
<222> LOCATION: (6)..(7)
<223> OTHER INFORMATION: Xaa can be any amino acid
<220> FEATURE:
<221> NAME/KEY: MISC_FEATURE
<222> LOCATION: (10)..(10)
<223> OTHER INFORMATION: Xaa can be any amino acid
<220> FEATURE:
<221> NAME/KEY: MISC_FEATURE
<222> LOCATION: (12)..(12)
<223> OTHER INFORMATION: Xaa can be any amino acid

<400> SEQUENCE: 8
```

Xaa Thr Xaa Tyr Leu Xaa Xaa Leu His Xaa Leu Xaa
1               5                   10

<210> SEQ ID NO 9
<211> LENGTH: 12
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Xaa can be any amino acid
<220> FEATURE:
<221> NAME/KEY: MISC_FEATURE
<222> LOCATION: (6)..(6)
<223> OTHER INFORMATION: Xaa can be any amino acid

<400> SEQUENCE: 9

Xaa Thr Arg Tyr Leu Xaa Gln Leu His Lys Leu Tyr
1               5                   10

<210> SEQ ID NO 10
<211> LENGTH: 13
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Xaa can be any amino acid
<220> FEATURE:
<221> NAME/KEY: MISC_FEATURE
<222> LOCATION: (3)..(3)
<223> OTHER INFORMATION: Xaa can be any amino acid
<220> FEATURE:
<221> NAME/KEY: MISC_FEATURE
<222> LOCATION: (6)..(7)
<223> OTHER INFORMATION: Xaa can be any amino acid
<220> FEATURE:
<221> NAME/KEY: MISC_FEATURE
<222> LOCATION: (10)..(10)
<223> OTHER INFORMATION: Xaa can be any amino acid
<220> FEATURE:
<221> NAME/KEY: MISC_FEATURE
<222> LOCATION: (12)..(13)
<223> OTHER INFORMATION: Xaa can be any amino acid

<400> SEQUENCE: 10

Xaa Thr Xaa Tyr Leu Xaa Xaa Leu His Xaa Leu Xaa Xaa
1               5                   10

<210> SEQ ID NO 11
<211> LENGTH: 13
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Xaa can be any amino acid
<220> FEATURE:
<221> NAME/KEY: MISC_FEATURE
<222> LOCATION: (6)..(6)
<223> OTHER INFORMATION: Xaa can be any amino acid
<220> FEATURE:
<221> NAME/KEY: MISC_FEATURE
<222> LOCATION: (13)..(13)
<223> OTHER INFORMATION: Xaa can be any amino acid

<400> SEQUENCE: 11

```
Xaa Thr Arg Tyr Leu Xaa Gln Leu His Lys Leu Tyr Xaa
1               5                   10
```

<210> SEQ ID NO 12
<211> LENGTH: 14
<212> TYPE: PRT
<213> ORGANISM: Artificial Sequence
<220> FEATURE:
<223> OTHER INFORMATION: Synthetic

<400> SEQUENCE: 12

```
Leu Asp Thr Arg Tyr Leu Glu Gln Leu His Gln Leu Tyr Ser
1               5                   10
```

<210> SEQ ID NO 13
<211> LENGTH: 13
<212> TYPE: PRT
<213> ORGANISM: Artificial Sequence
<220> FEATURE:
<223> OTHER INFORMATION: Synthetic

<400> SEQUENCE: 13

```
Asp Thr Arg Tyr Leu Glu Gln Leu His Lys Leu Tyr Ser
1               5                   10
```

<210> SEQ ID NO 14
<211> LENGTH: 14
<212> TYPE: PRT
<213> ORGANISM: Artificial Sequence
<220> FEATURE:
<223> OTHER INFORMATION: Synthetic

<400> SEQUENCE: 14

```
Leu Asp Thr Arg Tyr Leu Glu Gln Leu His Lys Leu Tyr Ser
1               5                   10
```

<210> SEQ ID NO 15
<211> LENGTH: 13
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (12)..(12)
<223> OTHER INFORMATION: Xaa = 4-cyano phenylalanine

<400> SEQUENCE: 15

```
Asp Thr Arg Tyr Leu Glu Gln Leu His Lys Leu Xaa Ser
1               5                   10
```

<210> SEQ ID NO 16
<211> LENGTH: 13
<212> TYPE: PRT
<213> ORGANISM: Artificial Sequence
<220> FEATURE:
<223> OTHER INFORMATION: Synthetic

<400> SEQUENCE: 16

```
Asp Thr Lys Tyr Leu Glu Gln Leu His Lys Leu Tyr Ser
1               5                   10
```

<210> SEQ ID NO 17
<211> LENGTH: 13
<212> TYPE: PRT
<213> ORGANISM: Artificial Sequence
<220> FEATURE:
<223> OTHER INFORMATION: Synthetic

<400> SEQUENCE: 17

Asp Thr Arg Tyr Leu Gln Glu Leu His Lys Leu Tyr Ser
1               5                   10

<210> SEQ ID NO 18
<211> LENGTH: 13
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (10)..(10)
<223> OTHER INFORMATION: Xaa = diaminobutyric acid

<400> SEQUENCE: 18

Asp Thr Arg Tyr Leu Glu Gln Leu His Xaa Leu Tyr Ser
1               5                   10

<210> SEQ ID NO 19
<211> LENGTH: 22
<212> TYPE: PRT
<213> ORGANISM: Artificial Sequence
<220> FEATURE:
<223> OTHER INFORMATION: Synthetic

<400> SEQUENCE: 19

Ala Gln Trp Asn Gln Leu Gln Gln Leu Asp Thr Arg Tyr Leu Glu Gln
1               5                   10                  15

Leu His Gln Leu Tyr Ser
            20

<210> SEQ ID NO 20
<211> LENGTH: 13
<212> TYPE: PRT
<213> ORGANISM: Artificial Sequence
<220> FEATURE:
<223> OTHER INFORMATION: Synthetic

<400> SEQUENCE: 20

Leu Asp Thr Arg Tyr Leu Glu Gln Leu His Lys Leu Tyr
1               5                   10

<210> SEQ ID NO 21
<211> LENGTH: 12
<212> TYPE: PRT
<213> ORGANISM: Artificial Sequence
<220> FEATURE:
<223> OTHER INFORMATION: Synthetic

<400> SEQUENCE: 21

Asp Thr Arg Tyr Leu Glu Gln Leu His Lys Leu Tyr
1               5                   10

<210> SEQ ID NO 22
<211> LENGTH: 12
<212> TYPE: PRT
<213> ORGANISM: Artificial Sequence
<220> FEATURE:
<223> OTHER INFORMATION: Synthetic

<400> SEQUENCE: 22

Asp Thr Arg Tyr Leu Glu Gln Leu His Lys Leu Tyr
1               5                   10

```
<210> SEQ ID NO 23
<211> LENGTH: 13
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (11)..(11)
<223> OTHER INFORMATION: Xaa = diaminobutyric acid

<400> SEQUENCE: 23

Leu Asp Thr Arg Tyr Leu Glu Gln Leu His Xaa Leu Tyr
1               5                   10

<210> SEQ ID NO 24
<211> LENGTH: 12
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (10)..(10)
<223> OTHER INFORMATION: Xaa = diaminobutyric acid

<400> SEQUENCE: 24

Asp Thr Arg Tyr Leu Glu Gln Leu His Xaa Leu Tyr
1               5                   10

<210> SEQ ID NO 25
<211> LENGTH: 13
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (11)..(11)
<223> OTHER INFORMATION: Xaa = diaminobutyric acid

<400> SEQUENCE: 25

Leu Asp Thr Lys Tyr Leu Glu Gln Leu His Xaa Leu Tyr
1               5                   10

<210> SEQ ID NO 26
<211> LENGTH: 12
<212> TYPE: PRT
<213> ORGANISM: Artificial Sequence
<220> FEATURE:
<223> OTHER INFORMATION: Synthetic

<400> SEQUENCE: 26

Asp Thr Arg Tyr Leu Glu Gln Leu His Ala Leu Tyr
1               5                   10

<210> SEQ ID NO 27
<211> LENGTH: 12
<212> TYPE: PRT
<213> ORGANISM: Artificial Sequence
<220> FEATURE:
<223> OTHER INFORMATION: Synthetic

<400> SEQUENCE: 27

Asp Thr Arg Tyr Leu Glu Gln Leu His Glu Leu Tyr
1               5                   10

<210> SEQ ID NO 28
<211> LENGTH: 12
```

<212> TYPE: PRT
<213> ORGANISM: Artificial Sequence
<220> FEATURE:
<223> OTHER INFORMATION: Synthetic

<400> SEQUENCE: 28

Ala Thr Arg Tyr Leu Glu Gln Leu His Lys Leu Tyr
1               5                   10

<210> SEQ ID NO 29
<211> LENGTH: 12
<212> TYPE: PRT
<213> ORGANISM: Artificial Sequence
<220> FEATURE:
<223> OTHER INFORMATION: Synthetic

<400> SEQUENCE: 29

Asp Thr Lys Tyr Leu Glu Gln Leu His Lys Leu Tyr
1               5                   10

<210> SEQ ID NO 30
<211> LENGTH: 14
<212> TYPE: PRT
<213> ORGANISM: Artificial Sequence
<220> FEATURE:
<223> OTHER INFORMATION: Synthetic

<400> SEQUENCE: 30

Asp Thr Lys Tyr Leu Glu Gln Leu His Lys Leu Tyr Lys Lys
1               5                   10

<210> SEQ ID NO 31
<211> LENGTH: 12
<212> TYPE: PRT
<213> ORGANISM: Artificial Sequence
<220> FEATURE:
<223> OTHER INFORMATION: Synthetic

<400> SEQUENCE: 31

Asp Thr Lys Tyr Cys Glu Gln Leu Lys Lys Leu Tyr
1               5                   10

<210> SEQ ID NO 32
<211> LENGTH: 14
<212> TYPE: PRT
<213> ORGANISM: Artificial Sequence
<220> FEATURE:
<223> OTHER INFORMATION: Synthetic

<400> SEQUENCE: 32

Asp Thr Lys Tyr Cys Glu Gln Leu Lys Lys Leu Tyr Lys Lys
1               5                   10

<210> SEQ ID NO 33
<211> LENGTH: 12
<212> TYPE: PRT
<213> ORGANISM: Artificial Sequence
<220> FEATURE:
<223> OTHER INFORMATION: Synthetic

<400> SEQUENCE: 33

Asp Thr Lys Cys Leu Glu Gln Lys His Lys Leu Tyr
1               5                   10

<210> SEQ ID NO 34
<211> LENGTH: 14
<212> TYPE: PRT

<213> ORGANISM: Artificial Sequence
<220> FEATURE:
<223> OTHER INFORMATION: Synthetic

<400> SEQUENCE: 34

Asp Thr Lys Cys Leu Glu Gln Lys His Lys Leu Tyr Lys Lys
1               5                   10

<210> SEQ ID NO 35
<211> LENGTH: 12
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Xaa can be any amino acid
<220> FEATURE:
<221> NAME/KEY: MISC_FEATURE
<222> LOCATION: (3)..(3)
<223> OTHER INFORMATION: Xaa can be any amino acid
<220> FEATURE:
<221> NAME/KEY: MISC_FEATURE
<222> LOCATION: (6)..(7)
<223> OTHER INFORMATION: Xaa can be any amino acid
<220> FEATURE:
<221> NAME/KEY: MISC_FEATURE
<222> LOCATION: (10)..(10)
<223> OTHER INFORMATION: Xaa can be any amino acid
<220> FEATURE:
<221> NAME/KEY: MISC_FEATURE
<222> LOCATION: (12)..(12)
<223> OTHER INFORMATION: Xaa can be any amino acid

<400> SEQUENCE: 35

Xaa Leu Xaa His Leu Xaa Xaa Leu Tyr Xaa Thr Xaa
1               5                   10

<210> SEQ ID NO 36
<211> LENGTH: 12
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (7)..(7)
<223> OTHER INFORMATION: Xaa can be any amino acid
<220> FEATURE:
<221> NAME/KEY: MISC_FEATURE
<222> LOCATION: (12)..(12)
<223> OTHER INFORMATION: Xaa can be any amino acid

<400> SEQUENCE: 36

Tyr Leu Lys His Leu Gln Xaa Leu Tyr Arg Thr Xaa
1               5                   10

<210> SEQ ID NO 37
<211> LENGTH: 13
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(2)
<223> OTHER INFORMATION: Xaa can be any amino acid
<220> FEATURE:
<221> NAME/KEY: MISC_FEATURE
<222> LOCATION: (4)..(4)
<223> OTHER INFORMATION: Xaa can be any amino acid
<220> FEATURE:

```
<221> NAME/KEY: MISC_FEATURE
<222> LOCATION: (7)..(8)
<223> OTHER INFORMATION: Xaa can be any amino acid
<220> FEATURE:
<221> NAME/KEY: MISC_FEATURE
<222> LOCATION: (11)..(11)
<223> OTHER INFORMATION: Xaa can be any amino acid
<220> FEATURE:
<221> NAME/KEY: MISC_FEATURE
<222> LOCATION: (13)..(13)
<223> OTHER INFORMATION: Xaa can be any amino acid

<400> SEQUENCE: 37

Xaa Xaa Leu Xaa His Leu Xaa Xaa Leu Tyr Xaa Thr Xaa
1               5                   10

<210> SEQ ID NO 38
<211> LENGTH: 13
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Xaa can be any amino acid
<220> FEATURE:
<221> NAME/KEY: MISC_FEATURE
<222> LOCATION: (8)..(8)
<223> OTHER INFORMATION: Xaa can be any amino acid
<220> FEATURE:
<221> NAME/KEY: MISC_FEATURE
<222> LOCATION: (13)..(13)
<223> OTHER INFORMATION: Xaa can be any amino acid

<400> SEQUENCE: 38

Xaa Tyr Leu Lys His Leu Gln Xaa Leu Tyr Arg Thr Xaa
1               5                   10

<210> SEQ ID NO 39
<211> LENGTH: 12
<212> TYPE: PRT
<213> ORGANISM: Artificial Sequence
<220> FEATURE:
<223> OTHER INFORMATION: Synthetic

<400> SEQUENCE: 39

Tyr Leu Lys His Leu Gln Glu Leu Tyr Arg Thr Asp
1               5                   10

<210> SEQ ID NO 40
<211> LENGTH: 15
<212> TYPE: PRT
<213> ORGANISM: Artificial Sequence
<220> FEATURE:
<223> OTHER INFORMATION: Synthetic

<400> SEQUENCE: 40

Ile Gln Arg Tyr Leu Lys His Leu Gln Glu Leu Tyr Arg Thr Asp
1               5                   10                  15

<210> SEQ ID NO 41
<211> LENGTH: 15
<212> TYPE: PRT
<213> ORGANISM: Artificial Sequence
<220> FEATURE:
<223> OTHER INFORMATION: Synthetic

<400> SEQUENCE: 41

Ile Gln Lys Tyr Leu Lys His Leu Gln Glu Leu Tyr Arg Thr Asp
```

-continued

```
1               5                   10                  15
```

<210> SEQ ID NO 42
<211> LENGTH: 13
<212> TYPE: PRT
<213> ORGANISM: Artificial Sequence
<220> FEATURE:
<223> OTHER INFORMATION: Synthetic

<400> SEQUENCE: 42

```
Gln Arg Tyr Leu Lys His Leu Gln Glu Leu Tyr Arg Thr
1               5                   10
```

<210> SEQ ID NO 43
<211> LENGTH: 13
<212> TYPE: PRT
<213> ORGANISM: Artificial Sequence
<220> FEATURE:
<223> OTHER INFORMATION: Synthetic

<400> SEQUENCE: 43

```
Arg Tyr Leu Lys His Leu Gln Glu Leu Tyr Arg Thr Asp
1               5                   10
```

<210> SEQ ID NO 44
<211> LENGTH: 14
<212> TYPE: PRT
<213> ORGANISM: Artificial Sequence
<220> FEATURE:
<223> OTHER INFORMATION: Synthetic

<400> SEQUENCE: 44

```
Gln Lys Tyr Leu Lys His Leu Gln Glu Leu Tyr Arg Thr Asp
1               5                   10
```

<210> SEQ ID NO 45
<211> LENGTH: 13
<212> TYPE: PRT
<213> ORGANISM: Artificial Sequence
<220> FEATURE:
<223> OTHER INFORMATION: Synthetic

<400> SEQUENCE: 45

```
Lys Tyr Leu Lys His Leu Gln Glu Leu Tyr Arg Thr Asp
1               5                   10
```

<210> SEQ ID NO 46
<211> LENGTH: 12
<212> TYPE: PRT
<213> ORGANISM: Artificial Sequence
<220> FEATURE:
<223> OTHER INFORMATION: Synthetic

<400> SEQUENCE: 46

```
Tyr Leu Lys His Leu Gln Gln Leu Tyr Arg Thr Asp
1               5                   10
```

<210> SEQ ID NO 47
<211> LENGTH: 15
<212> TYPE: PRT
<213> ORGANISM: Artificial Sequence
<220> FEATURE:
<223> OTHER INFORMATION: Synthetic

<400> SEQUENCE: 47

```
Ile Gln Arg Tyr Leu Lys His Leu Gln Gln Leu Tyr Arg Thr Asp
1               5                   10                  15
```

```
<210> SEQ ID NO 48
<211> LENGTH: 12
<212> TYPE: PRT
<213> ORGANISM: Artificial Sequence
<220> FEATURE:
<223> OTHER INFORMATION: Synthetic

<400> SEQUENCE: 48

Tyr Leu Lys His Leu Gln Gln Leu Tyr Arg Thr Asn
1               5                   10

<210> SEQ ID NO 49
<211> LENGTH: 15
<212> TYPE: PRT
<213> ORGANISM: Artificial Sequence
<220> FEATURE:
<223> OTHER INFORMATION: Synthetic

<400> SEQUENCE: 49

Ile Gln Arg Tyr Leu Lys His Leu Gln Gln Leu Tyr Arg Thr Asn
1               5                   10                  15

<210> SEQ ID NO 50
<211> LENGTH: 12
<212> TYPE: PRT
<213> ORGANISM: Artificial Sequence
<220> FEATURE:
<223> OTHER INFORMATION: Synthetic

<400> SEQUENCE: 50

Tyr Leu Lys His Leu Gln Glu Leu Tyr Arg Thr Asp
1               5                   10

<210> SEQ ID NO 51
<211> LENGTH: 15
<212> TYPE: PRT
<213> ORGANISM: Artificial Sequence
<220> FEATURE:
<223> OTHER INFORMATION: Synthetic

<400> SEQUENCE: 51

Gln Arg Tyr Leu Lys His Leu Gln Glu Leu Tyr Arg Thr Asp Leu
1               5                   10                  15

<210> SEQ ID NO 52
<211> LENGTH: 12
<212> TYPE: PRT
<213> ORGANISM: Artificial Sequence
<220> FEATURE:
<223> OTHER INFORMATION: Synthetic

<400> SEQUENCE: 52

Tyr Leu Lys His Leu Gln Gln Leu Tyr Arg Thr Asn
1               5                   10

<210> SEQ ID NO 53
<211> LENGTH: 12
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (10)..(10)
<223> OTHER INFORMATION: Xaa can be any amino acid

<400> SEQUENCE: 53
```

Asp Ser Lys Phe Leu Glu Gln Val His Xaa Leu Tyr
1               5                   10

<210> SEQ ID NO 54
<211> LENGTH: 12
<212> TYPE: PRT
<213> ORGANISM: Artificial Sequence
<220> FEATURE:
<223> OTHER INFORMATION: Synthetic

<400> SEQUENCE: 54

Asp Ser Lys Phe Leu Glu Gln Val His Lys Leu Tyr
1               5                   10

<210> SEQ ID NO 55
<211> LENGTH: 16
<212> TYPE: PRT
<213> ORGANISM: Artificial Sequence
<220> FEATURE:
<223> OTHER INFORMATION: Synthetic

<400> SEQUENCE: 55

Asp Ser Lys Phe Leu Glu Gln Val His Lys Leu Tyr Arg Gln Ile Lys
1               5                   10                  15

<210> SEQ ID NO 56
<211> LENGTH: 12
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (3)..(3)
<223> OTHER INFORMATION: Xaa can be any amino acid

<400> SEQUENCE: 56

Tyr Leu Xaa His Val Gln Glu Leu Phe Lys Ser Asp
1               5                   10

<210> SEQ ID NO 57
<211> LENGTH: 12
<212> TYPE: PRT
<213> ORGANISM: Artificial Sequence
<220> FEATURE:
<223> OTHER INFORMATION: Synthetic

<400> SEQUENCE: 57

Tyr Leu Lys His Val Gln Glu Leu Phe Lys Ser Asp
1               5                   10

<210> SEQ ID NO 58
<211> LENGTH: 15
<212> TYPE: PRT
<213> ORGANISM: Artificial Sequence
<220> FEATURE:
<223> OTHER INFORMATION: Synthetic

<400> SEQUENCE: 58

Ile Gln Arg Tyr Leu Lys His Val Gln Glu Leu Phe Lys Ser Asp
1               5                   10                  15

<210> SEQ ID NO 59
<211> LENGTH: 15
<212> TYPE: PRT
<213> ORGANISM: Artificial Sequence
<220> FEATURE:

<223> OTHER INFORMATION: Synthetic

<400> SEQUENCE: 59

Ile Gln Lys Tyr Leu Lys His Val Gln Glu Leu Phe Lys Ser Asp
1               5                   10                  15

<210> SEQ ID NO 60
<211> LENGTH: 12
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (3)..(3)
<223> OTHER INFORMATION: Xaa can be any amino acid
<220> FEATURE:
<221> NAME/KEY: MISC_FEATURE
<222> LOCATION: (6)..(6)
<223> OTHER INFORMATION: Xaa can be any amino acid
<220> FEATURE:
<221> NAME/KEY: MISC_FEATURE
<222> LOCATION: (8)..(8)
<223> OTHER INFORMATION: Xaa can be any amino acid
<220> FEATURE:
<221> NAME/KEY: MISC_FEATURE
<222> LOCATION: (10)..(10)
<223> OTHER INFORMATION: Xaa can be any amino acid

<400> SEQUENCE: 60

Gln Gly Xaa Ala Leu Xaa Gln Xaa Gln Xaa Leu Tyr
1               5                   10

<210> SEQ ID NO 61
<211> LENGTH: 12
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (8)..(8)
<223> OTHER INFORMATION: Xaa can be any amino acid

<400> SEQUENCE: 61

Gln Gly Asp Ala Leu Arg Gln Xaa Gln Val Leu Tyr
1               5                   10

<210> SEQ ID NO 62
<211> LENGTH: 12
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (8)..(8)
<223> OTHER INFORMATION: Xaa = norleucine

<400> SEQUENCE: 62

Gln Gly Asp Ala Leu Arg Gln Xaa Gln Val Leu Tyr
1               5                   10

<210> SEQ ID NO 63
<211> LENGTH: 16
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (8)..(8)
<223> OTHER INFORMATION: Xaa = norleucine

<400> SEQUENCE: 63

Gln Gly Asp Ala Leu Arg Gln Xaa Gln Val Leu Tyr Arg Gln Ile Lys
1               5                   10                  15

<210> SEQ ID NO 64
<211> LENGTH: 13
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (9)..(9)
<223> OTHER INFORMATION: Xaa = norleucine

<400> SEQUENCE: 64

Leu Gln Gly Asp Ala Leu Arg Gln Xaa Gln Val Leu Tyr
1               5                   10

<210> SEQ ID NO 65
<211> LENGTH: 17
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (9)..(9)
<223> OTHER INFORMATION: Xaa = norleucine

<400> SEQUENCE: 65

Leu Gln Gly Asp Ala Leu Arg Gln Xaa Gln Val Leu Tyr Arg Gln Ile
1               5                   10                  15

Lys

<210> SEQ ID NO 66
<211> LENGTH: 12
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (3)..(3)
<223> OTHER INFORMATION: Xaa can be any amino acid
<220> FEATURE:
<221> NAME/KEY: MISC_FEATURE
<222> LOCATION: (5)..(5)
<223> OTHER INFORMATION: Xaa can be any amino acid
<220> FEATURE:
<221> NAME/KEY: MISC_FEATURE
<222> LOCATION: (7)..(7)
<223> OTHER INFORMATION: Xaa can be any amino acid
<220> FEATURE:
<221> NAME/KEY: MISC_FEATURE
<222> LOCATION: (10)..(10)
<223> OTHER INFORMATION: Xaa can be any amino acid

<400> SEQUENCE: 66

Tyr Leu Xaa Gln Xaa Gln Xaa Leu Ala Xaa Gly Gln
1               5                   10

<210> SEQ ID NO 67
<211> LENGTH: 12
<212> TYPE: PRT
<213> ORGANISM: Artificial Sequence
<220> FEATURE:

```
<223> OTHER INFORMATION: Synthetic
<220> FEATURE:
<221> NAME/KEY: MISC_FEATURE
<222> LOCATION: (5)..(5)
<223> OTHER INFORMATION: Xaa can be any amino acid

<400> SEQUENCE: 67

Tyr Leu Val Gln Xaa Gln Arg Leu Ala Asp Gly Gln
1               5                   10

<210> SEQ ID NO 68
<211> LENGTH: 12
<212> TYPE: PRT
<213> ORGANISM: Artificial Sequence
<220> FEATURE:
<223> OTHER INFORMATION: Synthetic

<400> SEQUENCE: 68

Asp Ser Pro Phe Gln Asp Gln Leu His Gln Leu Tyr
1               5                   10

<210> SEQ ID NO 69
<211> LENGTH: 12
<212> TYPE: PRT
<213> ORGANISM: Artificial Sequence
<220> FEATURE:
<223> OTHER INFORMATION: Synthetic

<400> SEQUENCE: 69

Tyr Leu Gln His Leu Gln Asp Gln Phe Pro Ser Asp
1               5                   10

<210> SEQ ID NO 70
<211> LENGTH: 12
<212> TYPE: PRT
<213> ORGANISM: Artificial Sequence
<220> FEATURE:
<223> OTHER INFORMATION: Synthetic

<400> SEQUENCE: 70

Glu Ile Lys Phe Leu Glu Gln Val Asp Gln Phe Tyr
1               5                   10

<210> SEQ ID NO 71
<211> LENGTH: 12
<212> TYPE: PRT
<213> ORGANISM: Artificial Sequence
<220> FEATURE:
<223> OTHER INFORMATION: Synthetic

<400> SEQUENCE: 71

Tyr Phe Gln Asp Val Gln Glu Leu Phe Lys Ile Glu
1               5                   10

<210> SEQ ID NO 72
<211> LENGTH: 9
<212> TYPE: PRT
<213> ORGANISM: Artificial Sequence
<220> FEATURE:
<223> OTHER INFORMATION: Synthetic

<400> SEQUENCE: 72

Pro Pro Glu Lys Val Gln Arg Leu Tyr
1               5

<210> SEQ ID NO 73
<211> LENGTH: 9
```

```
<212> TYPE: PRT
<213> ORGANISM: Artificial Sequence
<220> FEATURE:
<223> OTHER INFORMATION: Synthetic

<400> SEQUENCE: 73

Tyr Leu Arg Gln Val Lys Glu Pro Pro
1               5

<210> SEQ ID NO 74
<211> LENGTH: 16
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (12)..(12)
<223> OTHER INFORMATION: Xaa = norleucine

<400> SEQUENCE: 74

Arg Gln Ile Lys Ile Trp Phe Pro Asn Arg Arg Xaa Lys Trp Lys Lys
1               5                   10                  15

<210> SEQ ID NO 75
<211> LENGTH: 13
<212> TYPE: PRT
<213> ORGANISM: Artificial Sequence
<220> FEATURE:
<223> OTHER INFORMATION: Synthetic

<400> SEQUENCE: 75

Leu Asp Ser Lys Phe Leu Glu Gln Val His Lys Leu Tyr
1               5                   10

<210> SEQ ID NO 76
<211> LENGTH: 12
<212> TYPE: PRT
<213> ORGANISM: Artificial Sequence
<220> FEATURE:
<223> OTHER INFORMATION: Synthetic

<400> SEQUENCE: 76

Asp Ser Lys Phe Leu Glu Gln Val His Lys Leu Tyr
1               5                   10

<210> SEQ ID NO 77
<211> LENGTH: 12
<212> TYPE: PRT
<213> ORGANISM: Artificial Sequence
<220> FEATURE:
<223> OTHER INFORMATION: Synthetic

<400> SEQUENCE: 77

Glu Ile Lys Phe Leu Glu Gln Val Asp Gln Phe Tyr
1               5                   10

<210> SEQ ID NO 78
<211> LENGTH: 13
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (9)..(9)
<223> OTHER INFORMATION: Xaa = norleucine (NLE)

<400> SEQUENCE: 78
```

```
Leu Gln Gly Asp Ala Leu Arg Gln Xaa Gln Val Leu Tyr
1               5                   10
```

```
<210> SEQ ID NO 79
<211> LENGTH: 4
<212> TYPE: PRT
<213> ORGANISM: Artificial Sequence
<220> FEATURE:
<223> OTHER INFORMATION: Synthetic

<400> SEQUENCE: 79

Arg Gln Ile Lys
1
```

```
<210> SEQ ID NO 80
<211> LENGTH: 4
<212> TYPE: PRT
<213> ORGANISM: Artificial Sequence
<220> FEATURE:
<223> OTHER INFORMATION: Synthetic

<400> SEQUENCE: 80

Lys Gln Ile Lys
1
```